(12) United States Patent  
Spears et al.

(10) Patent No.: US 11,908,154 B2  
(45) Date of Patent: Feb. 20, 2024

(54) SYSTEM AND METHOD FOR EVALUATING TUMOR STABILITY

(71) Applicant: Fibonacci Phyllotaxis Inc., Sacramento, CA (US)

(72) Inventors: Colin Paul Spears, Carmichael, CA (US); Stephanie Brower, Folsom, CA (US)

(73) Assignee: FIBONACCI PHYLLOTAXIS INC., Sacramento, CA (US)

(*) Notice: Subject to any disclaimer, the term of this patent is extended or adjusted under 35 U.S.C. 154(b) by 278 days.

(21) Appl. No.: 17/167,830

(22) Filed: Feb. 4, 2021

(65) Prior Publication Data

US 2022/0245848 A1    Aug. 4, 2022

(51) Int. Cl.
| | |
|---|---|
| G06T 7/62 | (2017.01) |
| G06T 7/00 | (2017.01) |
| A61B 5/00 | (2006.01) |
| A61B 5/103 | (2006.01) |
| A61B 5/107 | (2006.01) |

(52) U.S. Cl.
CPC .............. *G06T 7/62* (2017.01); *A61B 5/0022* (2013.01); *A61B 5/0077* (2013.01); *A61B 5/103* (2013.01); *A61B 5/6898* (2013.01); *A61B 5/742* (2013.01); *G06T 7/0014* (2013.01); *G06T 2207/10116* (2013.01); *G06T 2207/30096* (2013.01); *G06T 2207/30204* (2013.01)

(58) Field of Classification Search
None
See application file for complete search history.

(56) References Cited

U.S. PATENT DOCUMENTS

| | | | |
|---|---|---|---|
| 1,780,237 | A | 11/1930 | Leslie |
| 2,016,346 | A | 10/1935 | Smith |

(Continued)

FOREIGN PATENT DOCUMENTS

| | | |
|---|---|---|
| CN | 202143652 U | 2/2012 |
| CN | 104720816 A | 6/2015 |

(Continued)

OTHER PUBLICATIONS

International Search Report and Written Opinion; dated May 12, 2022; Application No. PCT/US2022/014494; Filed: Jan. 31, 2022; 18 pages.

(Continued)

*Primary Examiner* — Mohammed Rachedine  
(74) *Attorney, Agent, or Firm* — CANTOR COLBURN LLP

(57) ABSTRACT

A device for identifying a size doubling number of a lesion, having: a planar surface defining a data portion that includes data zones, including: a first zone that defines first zone arcs distributed in a concentric configuration, the first zone arcs defining first mutually unique radii, ranging from a first minimum radius to a first maximum radius; the first zone includes first zone size markers, respectively positioned adjacent ones of the first zone arcs, and the first zone size markers respectively identify the size doubling number of the clinical lesion having a size that corresponds to a respective one of the first zone arcs, the size doubling number being one or more of a volume doubling number, an area doubling number and a radius doubling number.

15 Claims, 9 Drawing Sheets

(56) References Cited

U.S. PATENT DOCUMENTS

| | | | |
|---|---|---|---|
| 2,557,428 A | 6/1951 | Grostic | |
| 4,131,998 A * | 1/1979 | Spears | A61B 5/107 |
| | | | 33/1 BB |
| 4,279,259 A * | 7/1981 | Lee | A41H 1/02 |
| | | | 600/587 |
| 4,389,782 A | 6/1983 | Webster | |
| 4,483,075 A | 11/1984 | Kundin | |
| D279,358 S | 6/1985 | Lichtman | |
| 4,944,737 A | 7/1990 | Bloom | |
| D322,125 S | 12/1991 | Dorsey | |
| D323,470 S | 1/1992 | Deyerle | |
| 5,102,391 A | 4/1992 | Palestrant | |
| D348,618 S | 7/1994 | Leslie et al. | |
| 5,741,212 A * | 4/1998 | Matthews | A61B 5/444 |
| | | | 600/300 |
| 6,215,893 B1 * | 4/2001 | Leshem | A61B 5/444 |
| | | | 382/128 |
| D496,596 S | 9/2004 | Dalrymple | |
| 7,124,760 B2 | 10/2006 | Wong | |
| 7,657,125 B2 | 2/2010 | Allen et al. | |
| D640,941 S | 7/2011 | Tucker | |
| 8,123,704 B2 | 2/2012 | Richards | |
| 9,218,661 B2 | 12/2015 | Gazit et al. | |
| D755,964 S | 5/2016 | Freudenthal | |
| D784,536 S | 4/2017 | Freudenthal | |
| D788,924 S | 6/2017 | Massad | |
| 9,696,897 B2 | 7/2017 | Garcia | |
| 10,169,882 B1 * | 1/2019 | Tokunaga | G06T 7/60 |
| 10,307,098 B2 | 6/2019 | Gareau | |
| 10,417,785 B2 | 9/2019 | Ghazizadeh | |
| D893,715 S | 8/2020 | Onorato | |
| 11,069,056 B2 * | 7/2021 | Perrin | G01N 33/57434 |
| 11,328,812 B2 * | 5/2022 | Masubuchi | G16H 30/40 |
| D956,976 S | 7/2022 | Onorato | |
| D960,362 S | 8/2022 | Dohmen | |
| 11,457,871 B2 * | 10/2022 | Lyman | G06T 7/0002 |
| 11,462,315 B2 * | 10/2022 | Rao | A61B 5/7267 |
| 2010/0091104 A1 | 4/2010 | Sprigle et al. | |
| 2013/0058546 A1 | 3/2013 | Di et al. | |
| 2018/0214070 A1 | 8/2018 | McDaniel | |
| 2019/0038135 A1 * | 2/2019 | Lee | A61B 3/12 |
| 2019/0294918 A1 | 9/2019 | Witchey et al. | |
| 2020/0211179 A1 * | 7/2020 | Sun | G06T 7/0012 |
| 2020/0294236 A1 * | 9/2020 | Kuroda | A61B 5/445 |
| 2020/0327670 A1 | 10/2020 | Connor | |

FOREIGN PATENT DOCUMENTS

| | | | | |
|---|---|---|---|---|
| CN | 106164929 A * | 11/2016 | | A61B 5/0022 |
| CN | 109044255 A * | 12/2018 | | A61B 1/2736 |
| CN | 110664411 A | 1/2020 | | |
| CN | 210521108 U | 5/2020 | | |
| EP | 1652472 A1 * | 5/2006 | | A61B 5/107 |
| EP | 1652472 A1 | 5/2006 | | |
| GB | 2164447 A | 3/1986 | | |
| TW | 202027090 A * | 7/2020 | | G06N 3/0454 |
| WO | WO-9523553 A1 * | 9/1995 | | A61B 10/00 |
| WO | 2011087807 A2 | 7/2011 | | |
| WO | WO-2017135564 A1 * | 8/2017 | | A61B 1/227 |
| WO | WO-2019092509 A1 * | 5/2019 | | |

OTHER PUBLICATIONS

Taiwan Office Action; dated Sep. 8, 2022; Application No. 111104169; 18 pages.

Collins et al., "Observations on Growth Rates of Human Tumors"; Am. J. Roentgenol. Radium Ther. Nucl. Med. Nov. 1956. 76 (5): 988-1000; PMID: 13362715.

Nishino et al., "Revised RECIST Guideline Version 1.1: What Oncologists Want to Know and What Radiologists Need to Know"; Downloaded from www.ajronline.org by 216.93.214.162 on Apr. 29, 2020 from IP address 216.93.214.162. Copyright ARRS.; 9 pages.

Schwartz et al., "Evaluation of Tumor Measurements in Oncology: Use of Film-Based and Electronic Techniques"; Journal of Clinical Oncology, vol. 18, No. 10 May 2000: pp. 2179-2184; Downloaded from ascopubs.org by Dr. Colin Spears on Aug. 27, 2020 from 216.093.214.162, Copyright © 2020 American Society of Clinical Oncology.

Spears, "Volume Doubling Measurement of Spherical and Ellipsoidal Tumors", Medical and Pediatric Oncology 12:212-217 (1984).

* cited by examiner

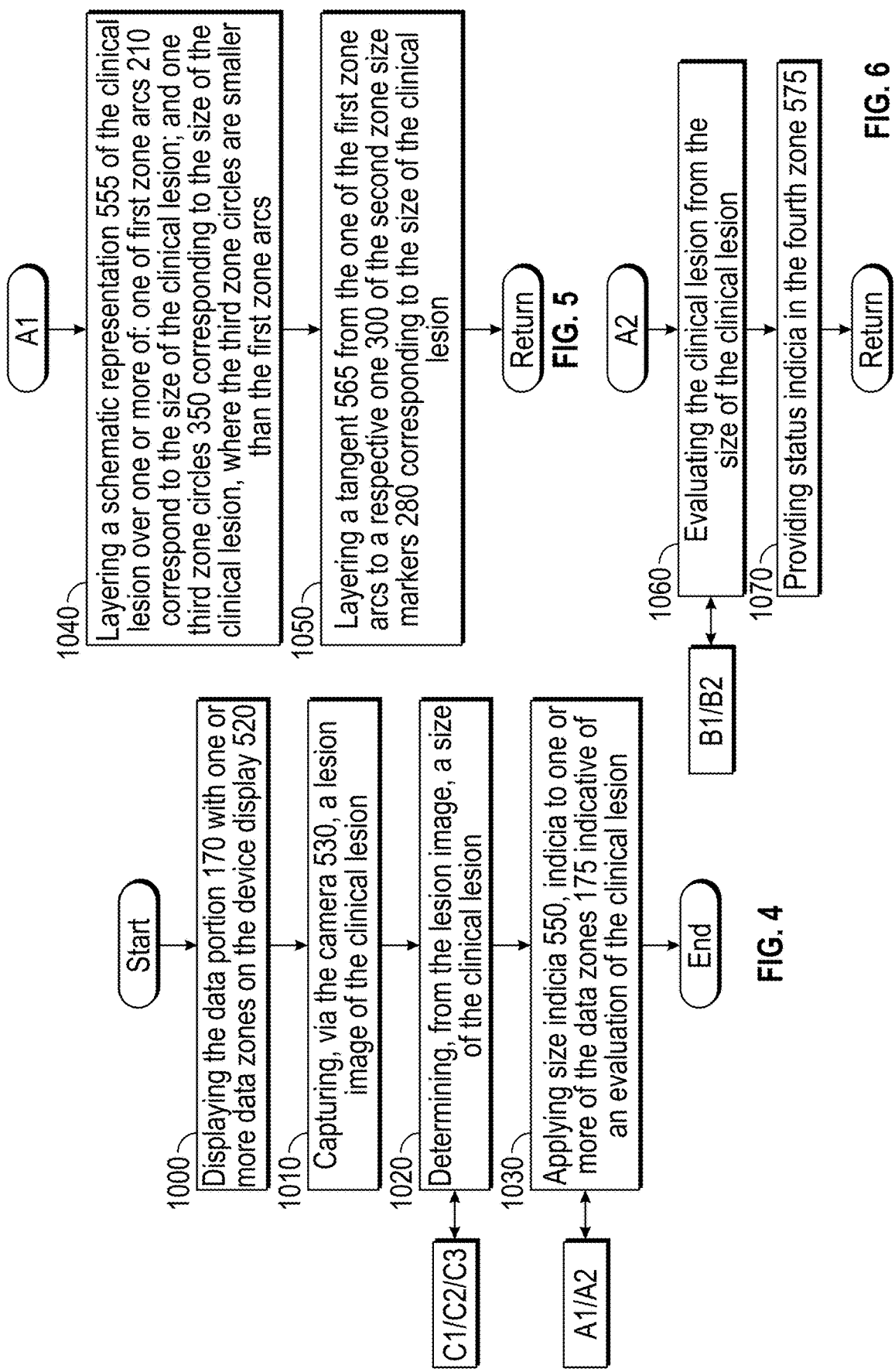

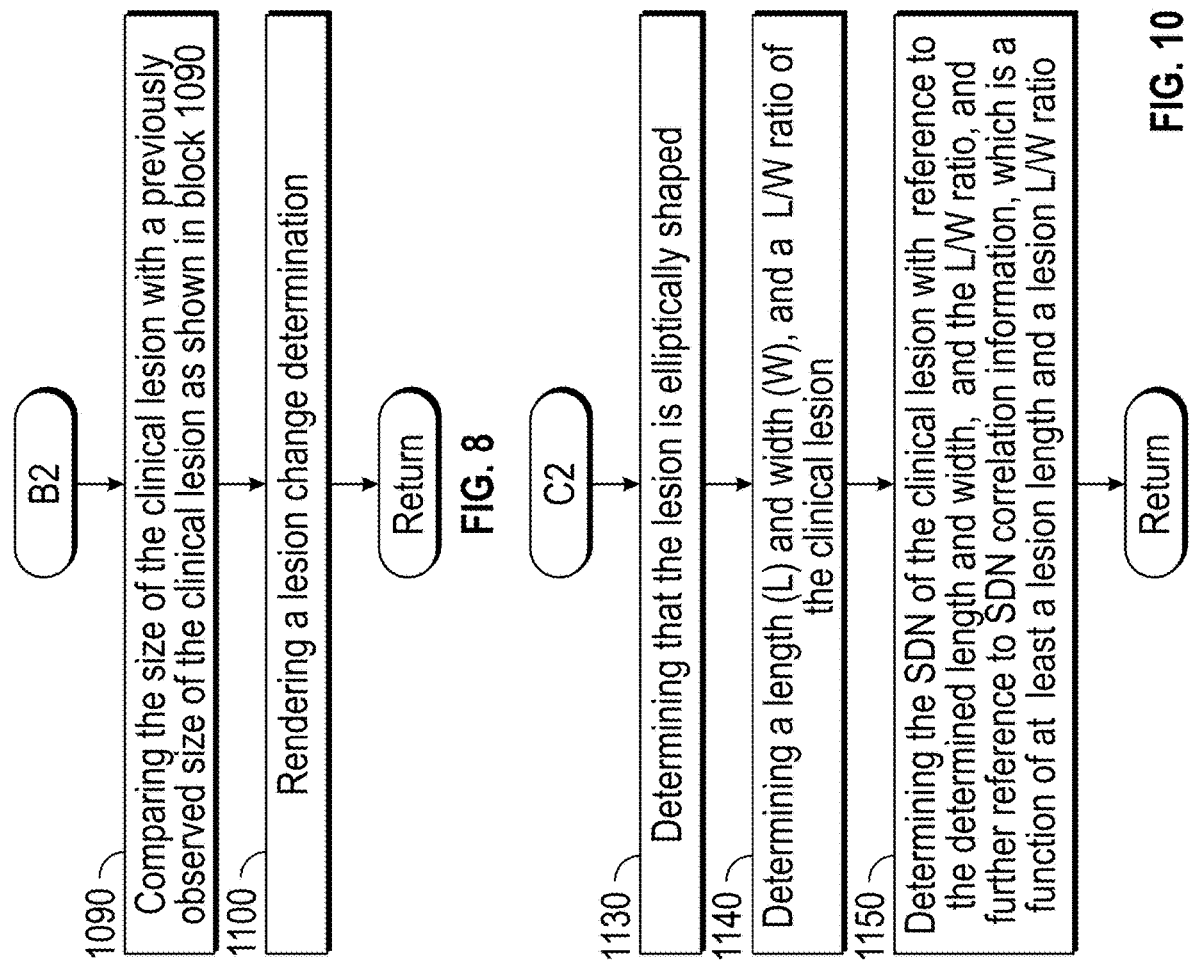
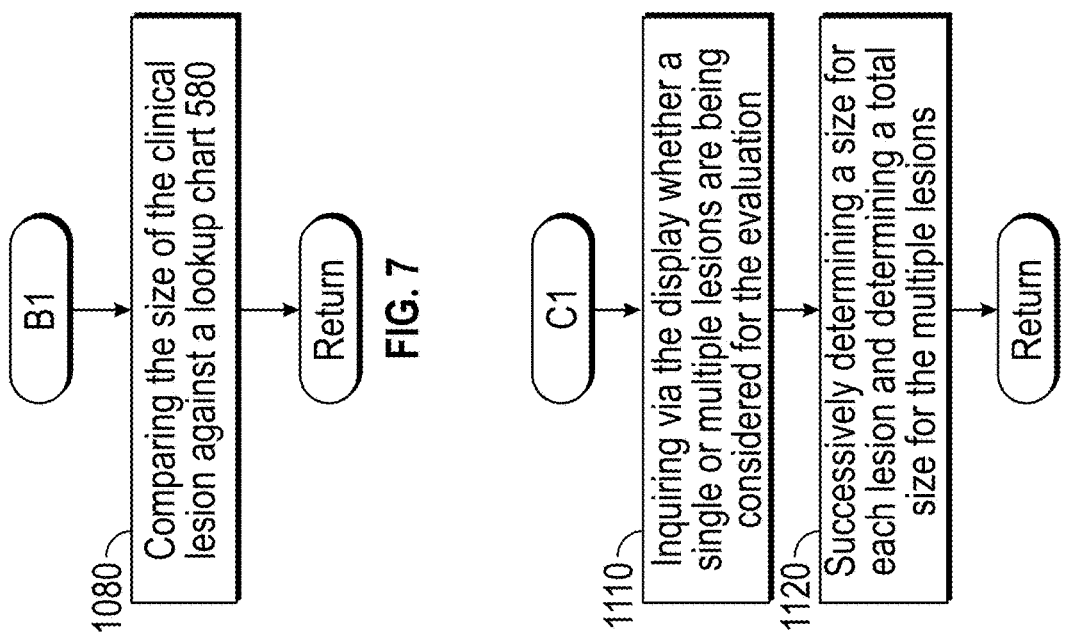

SYSTEM AND METHOD FOR EVALUATING TUMOR STABILITY

BACKGROUND

Exemplary embodiments pertain to the art of medical devices and more specifically for a system and method for evaluating tumor stability.

Volume doubling rulers may be used for rapid estimation of tumor volume using projection areas of single-plane images such as chest radiographs. The potential utility of the rulers derives in part from the convenient relationships that exist for the interconversion of volume, volume doubling number, and decimal log growth or cell kill.

BRIEF DESCRIPTION

A device for identifying a size doubling number of a clinical lesion relative to a predetermined size of the clinical lesion, the device including: a planar surface including a first planar surface end, the planar surface extending longitudinally aft from the first planar surface end to a second planar surface end; the planar surface defining a data portion first end that is adjacent the first planar surface end, and a data portion extending longitudinally aft from the data portion first end to a data portion second end, wherein the data portion includes data zones, including: a first zone defining a first zone first end that is adjacent the data portion first end, the first zone extending longitudinally aft from the first zone first end to a first zone second end, wherein: the first zone defines first zone arcs, the first zone arcs being distributed in a concentric configuration, the first zone arcs defining first mutually unique radiuses, ranging from a first minimum radius of a first zone first arc to a first maximum radius of a first zone last circle, and wherein a concentric center of the first zone arcs is adjacent the first zone first end; the first zone arcs are successively larger from each other by a predetermined multiplication factor; the first zone includes first zone size markers, respectively positioned adjacent ones of the first zone arcs, and the first zone size markers respectively identify the size doubling number of the clinical lesion having a size that corresponds to a respective one of the first zone arcs.

A method of evaluating a lesion with a smart device, including: displaying a data portion with one or more data zones on a device display of the smart device; capturing, via the camera, a lesion image of the clinical lesion; determining, from the lesion image, a size of the clinical lesion; and applying size indicia, indicia to one or more of the data zones indicative of an evaluation of the clinical lesion.

A device is disclosed for identifying a size doubling number of a lesion, having: a planar surface defining a data portion that includes data zones, including: a first zone that defines first zone arcs distributed in a concentric configuration, the first zone arcs defining first mutually unique radiuses, ranging from a first minimum radius to a first maximum radius; the first zone includes first zone size markers, respectively positioned adjacent ones of the first zone arcs, and the first zone size markers respectively identify the size doubling number of the clinical lesion having a size that corresponds to a respective one of the first zone arcs, the size doubling number being one or more of a volume doubling number, an area doubling number and a radius doubling number.

BRIEF DESCRIPTION OF THE DRAWINGS

The following descriptions should not be considered limiting in any way. With reference to the accompanying drawings, like elements are numbered alike:

FIG. 4 is a flowchart showing a method of evaluating a tumor stability with the device of FIG. 3, according to an embodiment; and FIGS. 5-11 are additional flowcharts showing additional aspects of the method of evaluating a tumor stability with the device of FIG. 3, according to an embodiment.

DETAILED DESCRIPTION

The system of evaluating tumor stability provides volume and area doubling devices as tools for measurement of clinical and radiographic tumor parameters of neoplastic disease with categorization of response to treatment, progression or stable disease. The embodiments provide a volume doubling number VDN (n), and area doubling number ADN (na), providing relatively rapid facile volumetric data using arc edges of diameter or cross sectional area edge tumors and other single vector measurements, from single radii (diameters), perpendicular cross sections, or cartesian (x, y, z) data. Volume doubling devices are useful for relatively rapid determination of volume or area doubling time, increase precision for categorization of stable disease, or determination of volume or area halving time (or response velocity). Relatively rapid assignment of tumors of a single doubling number enables relatively instantaneous determination of categories of tumor stability and comparison of different criteria of response or regression.

Figure 1A:
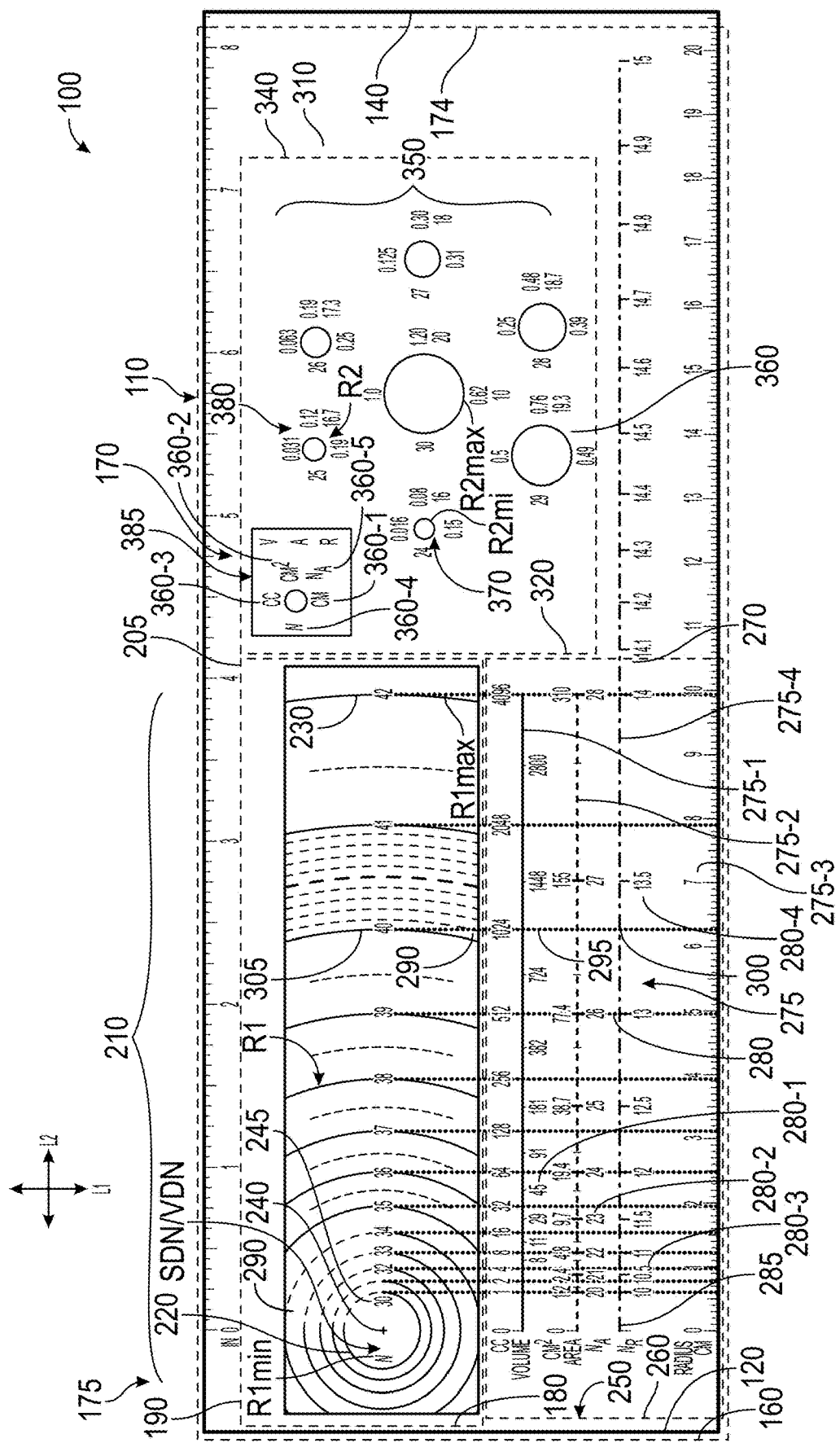
FIG. 1A is a device for evaluating a tumor stability, wherein the device is a ruler according to an embodiment.

Turning to FIG. 1A, an embodiment of a device 100 is disclosed for identifying a size doubling number (SDN) of a clinical lesion relative to a predetermined size, e.g., a single cell, of the clinical lesion. The SDN may be one or more of a volume doubling number (VDN), area doubling number (ADN) and radius doubling number (RDN), as indicated below. VDN is alternatively referred to herein as (n), (nv) or VDN (nv), ADN is alternatively referred to herein as (na) or ADN (na), and RDN is alternatively referred to herein as (nr) or RDN (nr). SDN may be used interchangeably herein for either of VDN, and ADN, the precise selection which shall be clear from the context. The device 100 of FIG. 1A may be formed of plastic and may define a ruler. The plastic may be transparent or translucent.

The device 100 may include a planar surface 110. The planar surface 110 may be rectangular and may be smaller in a lateral direction L1 (e.g., top-down) than a longitudinal direction L2 (e.g., left-right). The planar surface 110 may include a first planar surface end 120 (e.g., a left-side end). The planar surface 110 may extend longitudinally aft (e.g., left to right), from the first planar surface end 120 to a second planar surface end 140. The planar surface 110 may define a planar surface top end 112 and a planar surface bottom end 114.

The planar surface 110 may define a data portion first end 160 that is adjacent the first planar surface end 120. A data portion 170 may extend longitudinally aft from the data portion first end 160 to a data portion second end 174. The data portion 170 may include data zones 175.

The data zones 175 may include a first zone 180 defining a first zone first end 190. The first zone first end 190 may be adjacent the data portion first end 160. The first zone 180 may extend longitudinally aft from the first zone first end 190 to a first zone second end 205. The first zone 180 may include indicia that may define first zone arcs 210. The first zone arcs 210 may be shown as complete circles, e.g., arc 290 is provided as a circle, and while arc 305 is a portion of a circle, to accommodate a spacing/indicia configuration of the first zone 180. The arcs 305 (or arc segments) may be laterally aligned and longitudinally spaced apart from each other within the first zone 180, between the concentric center 240 and the first zone second end 205. That is, the first zone 180 may be rectangular having a boundary that truncates the first zone arcs 210 that would otherwise extend pas the boundary when forming circles.

The first zone arcs 210 are distributed in a concentric configuration. The first zone arcs 210 may define first mutually unique radiuses R1. The first unique radiuses R1 may range from a first minimum radius R1min of a first zone first arc 220, which is a complete circle, to a first maximum radius R1max of a first zone last circle 230. A concentric center 240 of the first zone arcs 210 may be adjacent the first zone first end 190.

The first zone arcs 210 may be successively larger relative to each other by a first multiplication factor of between 1.25-1.50. The first multiplication factor may be the cube root of 2 (for a volumetric related information shown in FIG. 1A) or square root (for area related information, e.g., shown in FIG. 1B).

The first zone 180 may include first zone size markers 245. The first zone size markers 245 may be respectively positioned adjacent ones of the first zone arcs 210. The first zone size markers 245 may respectively identify the size doubling numbers (SDN) of the clinical lesion having a size that corresponds to a respective one of the first zone arcs 210. In the embodiment of FIG. 1A, the size doubling numbers SDN are volume doubling number VDN, illustrated as n, representing successive volume doublings of the tumor compared to a single celled tumor. For example, 30 as the VDN represent 30 volume doublings, while 31 as the VDN represents 31 volume doublings.

The data zones 175 include a second zone 250. The second zone 250 is laterally adjacent and longitudinally aligned with the first zone 180. That is, the second zone 250 is between the first zone 180 and the planar surface bottom end 114. The second zone 250 defines a second zone first end 260 that is longitudinally adjacent the data portion first end 160. The second zone 250 extends longitudinally aft from the second zone first end 260 to a second zone second end 270.

The second zone 250 may include indicia that defines a graduated line gauge, generally identified as 275 and second zone size markers, generally identified as 280. The second zone size markers 280 may identify one or more of radius R, area A and volume V of the clinical lesion, and may further identify the SDN as indicated below.

The second zone 250 may be oriented such that a zero-mark 285 of the second zone size markers 280 is longitudinally aligned with the concentric center 240 of the first zone arcs 210. The first zone arcs 210 and graduated line gauge 275 may configured proportionally to each other, e.g., with a 1:1 scale.

More specifically, in FIG. 1A, there are three of the graduated line gauges 275-1, 275-2 and 275-3, each having second zone markers 280-1, 280-2, 280-3. The line gauges 275-1, 275-2 and 275-3 are laterally offset from each other and longitudinally aligned with each other and the first zone 180. The first graduated line gauge 275-1 is laterally closest to the first zone 180. Its markers 280-1, above and below the gauge, represent a cubic volume of the tumor. As can be seen, the first graduated line gauge 275-1 does not include volume doubling numbers VDN because such numbers are already in the first zone 180 to which it is aligned. The cubic volume is demarcated from 1 cc at 30 VDN to 4096 cc at 42 VDN. The second graduated line gauge 275-2 is laterally adjacent to the first graduated line gauge 275-1. Its markers 280-2 represent an area of the tumor, above the gauge, and an area doubling number ADN, below the gauge, for the tumor. The area markers are demarcated from 1.2 cm^2, at 1 cc, to 310 cm^2 at 4096 cc (as used herein the carrot ^represents an exponent, so that cm^2, e.g., represents square centimeters). The ADNs are demarcated from 20, corresponding to a 30 VDN, to 28, corresponding to a 42 VDN. The third graduated line gauge 275-3 is laterally adjacent to the second graduated line gauge 275-2. The third graduated line gauge 275-3 is adjacent to the planar surface bottom end 114. Its markers 280-3 represent a radius size of the tumor, and are incremented by 1 cm, between zero and 20 cm. RDN markers 280-4 are provided in an additional graduated line gauge 275-4 in the second zone, between the second and third graduated lines. The values of the device 100 identified herein are for reference and are not intended on limiting the scope of the embodiments.

In some embodiments, a supplemental graduated line gauge 288 is adjacent the planar surface top end 112 and extends longitudinally between the first and second planar surface ends 120, 140. With this configuration, the supplemental graduated line gauge 228 is laterally between the planar surface top end 112 and the first and third zones. For example, the third graduated line gauge 275-3 has the units of cm, and the supplemental graduated line gauge 288 has the units of inches. In addition, the third graduated line gauge 275-3 may extend longitudinally beyond the third zone to both the first and second planar surface ends 120, 140. This enables both the supplemental and third graduated line gauge to be utilized as measuring implements in a general sense. It is to be appreciated that in some embodiments, the first through third zones may utilize and be calibrated to inches rather than cm as the primary units, and supplemental graduated line gauge may utilize cm rather than inches as its primary units.

Thus, in the device 100 of FIG. 1A, one radius doubling is equivalent to two area doublings, which is equivalent to three volume doublings. This may be represented as 3VDN=2ADN=1RDN. RDN is the radius doubling number, which may alternatively be referred to herein as nr, and which is related to doubling of the true length identified in the third graduated line 275-3.

A size measurement of the clinical lesion is obtained by placing the device 100 over a tumor so that the center of the tumor is at the concentric center 240, providing the tumor is at least as large as VDN=30. That is, if the VDN was less than 30, the device 100 is used differently, as indicated below. Then, one of a plurality of tangents (or drop lines), generally labeled 295, is referenced, which extends laterally from a longitudinal outer diameter of the respective one of the circles 210 in the first zone arcs 210 to the radius line gauge 275-3. This measurement corresponds to a size of the clinical lesion to a respective one 300 of the second zone size markers 280. It is to be appreciated that the tangents 295 extend from a right side of the longitudinal outer diameter as shown in the figure, e.g., a side registering a larger radius for a given circle or arc in the first zone.

As indicated, the first zone first arc 220 represents $2^{n1}$ volume doublings relative to a single tumor cell of the clinical lesion. The first zone last circle 230 represents $2^{m1}$ volume doublings relative to the single tumor cell. In these expressions, $m1=n1+c1$. The variable $c1$ is the number of arcs in the first zone arcs 210. Further, $n1=30$, and $c1=10$ or greater. In the embodiment shown in FIG. 1A, $c1=12$. The first maximum radius R1max is between substantially 10 cm and the first minimum radius R1min is between substantially 0.5 cm and substantially 1 cm.

Thus, with further reference to the first and second zones 180, 250, one option of utilizing the device 100 includes measuring of the radius (or diameter divided by 2) of a parameter tumor or lesion is obtained using the radius line gauge 275-3, with the R=zero cm set point at the middle (centroid) of the lesion. An estimated volume in cc (cm^3) is recorded and the associated VDN (n) value using the drop lines 295. The volume is checked also in placing the concentric center 240 at the centroid of the lesion. Since cat (CT or computerized tomography) scans and magnetic resonance (MR), PET (Positron emission tomography) scans and ultrasound data usually have internal cm calibration for images smaller than real size, one can apply the radius (linear-cm) results to the device 100 for volume, area, and the VDN value. The circles and arcs defined by the first set of circles 210 can be used to check for a difference in VDN at any magnification and without numerical assignment.

Diameters (or double the radii) of lesions represent maximum values of the lesion under consideration, that is heuristically a maximal cross-section of the sphere or projection area of the radiographic image. This allows concurrent determination of the area in cm^2, and the area doubling number, ADN (nA), which is two-thirds of the volumetric VDN (n). It is to be appreciated that an outer surface area of a spherical lesion is 4 times its maximal cross-sectional area.

Accumulating volume doubling data from the device 100 over time will provide, e.g., a summation of total parameters of volume and volume doubling VDN (n) of a disease, around a body. Alternatively, a distribution of individual VDN (n) values and volumes may be considered. In some cases, a total body tumor burden volume, in cc, and VDN (n) numbers, may be considered, e.g., by summing the values for all lesions around a body, as indicated below. A volume doubling time (VDTime) may be obtained, and with negative or VDN ($-\Delta n$)(i.e., delta) values, a volume halving time (VHTime) or regression velocity (RV) may be calculated.

With further reference to FIG. 1A, a third zone 310 of the device defines a third zone first end 320 adjacent to the first zone second end 205. The third zone 310 extends longitudinally aft from the third zone first end 320 to a third zone second end 340. The third zone 310 includes indicia that defines third zone circles generally referred to as 350 and includes third zone size markers generally referred to as 360. The third zone circles 350 are distributed in a non-overlapping configuration and define second mutually unique radiuses R2 ranging from a second minimum radius R2 min of a third zone first circle 370 to a second maximum radius R2max of a third zone last circle 380.

Each successively larger circle in the third zone circles 350 is larger than each successively smaller circle in the third zone circles 350 by the first multiplication factor. The first minimum radius R1min of the first zone arcs 210 is the same as or greater than the second maximum radius R2max of the third zone circles 350. The third zone size markers 360 identify the size doubling number (SDN) of the clinical lesion having a size that corresponds to a respective one of the third zone circles 350. As indicated the SDNs for the embodiment in FIG. 1 are volume doubling number, VDNs (n).

Third zone size markers 360 may identify one or more of radius R, area A, volume V, volume doubling number VDN (n) and area doubling number ADN (na), of each of the third zone circles 350. As illustrated, each of these parameters is shown respectively as 360-1 through 360-5 in a key 385. In addition, the third zone circles 350 are arranged along a hexagram, with the largest circle being in the center of the hexagram, though this arrangement is not intended on limiting the scope of the embodiments.

The third zone first circle 370 represents $2^{n2}$ volume doublings of the single tumor cell relative to the clinical lesion. The third zone last circle 380 represents $2^{m2}$ volume doublings relative to the single tumor cell. In these expressions, $m2=n2+c2$. The variable $c2$ is the number of circles in the third zone circles 350. The variable $n2=24$, and $c2=7$ in FIG. 1A, though this is not intended on limiting the scope of the embodiments. The second maximum radius R2max is between substantially 0.5 cm and substantially 1 cm. The second minimum radius R2 min is substantially 0.15 cm. These values are not intended on limiting the scope of the disclosed embodiments. For continuity between using the first and second zones vs the third zone, the first minimum radius R1min and the second maximum radius R2max may be the same size as each other.

The third zone 310 shows an adaptation of the device 100 for relatively small lesions for volume and VDN measurement using full circles instead of arc segments of the first zone. The separation shown in the third zone 310 may allow assignment of a volume based on a single diameter (radius*2) with volume, VDN, area and ADN displayed per the key 385 in the third zone 310. The key 385 is adjacent to the first zone second end 205, near the planar surface top end 112.

Using tumor volume and VDN (n) values, several calculations result from setting n30≡1 cm3 (cc) with log 2=0.30103 (referenced below), with a few definitions: $\Delta n$ (delta-n) is the volumetric change in n over time; R is the radius; and A is area (the heuristic replacement of perpendicular cross-sectional products that as squares are relatively less biologic).

The range of the clinical parameter n, from an VDN (n) of 24 to VDN (n) of 42 is a 2~range, that is over a 10^5 order (100,000-fold) of magnitude of volume magnitude change, is displayed in FIG. 1A. Formulas [1a,1b] and [6] (below) are substantially exact, while formulas [2-5] are approximation formulas accurate to 2.4% (percent) spanning $\Delta n$ of 10 VDN, due to the fact that 2 is 1024 rather than 1000. Log is base 10. TI is the time interval of observation. The volume of a lesion corresponding to a VDN (n) of 27 is 0.125 cc with a radius of 0.31 cm, half of the reference VDN (n) of 30 radius and twice that of a VDN (n) of 24. VHTime is the volume halving time; RV is the response velocity, which is the time interval (TI) divided by the decrease in the VDN ($-\Delta n$).

Volume and VDN (n) values are interconvertible using formulas (2) and (3), below. In these formulas, where there are multiple lesions, a summation of the volumes, in cc (cm^3), of all parameter lesions together. A utilization of the volume markers (indicia) to obtain the estimated total VDN (n) value of the summed total volume. Tenths of decimals of a VDN (n) interval are shown at the 40-41st VDNs for reference.

$TI \div (+\Delta n) = $ VDTime for growing lesions  Formula [1a]:

$TI \div (-\Delta n) = $ VHTime or RV for shrinking lesions, e.g., a decrease in VDN $(n)$  Formula [1b]:

$\log(cm^3) = (0.3*n) - 9$  Formula [2]:

$n = [\log(cm^3) + 9] \div 0.3$  Formula [3]:

$0.3*(\pm \Delta n) = \log(\text{cell growth or cell kill})$  Formula [4]:

$0.3*n = \log(\text{cell number})$  Formula [5]:

$3*\Delta nv = 1*\Delta nr = 2*\Delta na$ for a given radius  Formula [6]:

The above formula [6] may be restated as: one doubling of radius RDN (nr) provides $3*\Delta n$ which is 3 volume doublings VDN (n). And a doubling of Area ADN (na) is exactly $1.5*\Delta n$, so that 2 consecutive area doublings also provide $3*\Delta n$. Formulas [2] and [3] are more precisely by substituting 9.0309 for 9, due to the fact that $2^{10}$ is 1024, not 1000.

With the inter-convertibility of single vector—diameter (radius), products of perpendicular diameters (areas) and volumes, the device 100 allows rapid comparison of major medically accepted approaches to tumor response in use. For the VDN (n), where a density of tumor cells per unit volume can be estimated, such as on pathology slide sections of a biopsy, a modification to cell number formulas is readily made, and in principle could be extended to stem cell counts as well. The radius (diameter/2) doubles RDN (nr) between n–24 to n–27 (in the third zone) and between n–27 to n–30 (in the third zone), providing a total of 6 volume doublings VDN (n) measurable in the third zone. The key 385 shows VDN (n) is at 9:00 o'clock (for a clock face laid over the layout in the third zone), volume is located at noon (cc), area in cm^2 at 3:00 o'clock (with its ADN (na), below), and radius at 6:00 o'clock for the respective circles.

When 3-dimensional objects are laid out on cartesian coordinates, parameter tumor lesions have relatively constant ratios of X, Y, and Z perpendicular vectors over time. Most lesions used as response parameters are typically semi-spherical, ovoid or ellipsoidal (discussed in greater detail, below, with respect to FIG. 2B). Orientation of 3 coordinate diameters typically remain fairly constant through growth, so that single diameter (radius) data will represent volumetric changes over time, both geometrically, and in clinical practice. The limit of length to width ratios under 1.6 using 2 diameters (perpendicular) results in a relatively similar volume data regardless of the method of calculating a third dimension. Thus, the device 100 remains relatively reliable for tumors that it can measure.

The device 100 allows clinicians and investigators to readily compare seemingly diverse criteria for tumor response and progression, and report outcome using the several methods side-by-side. The device 100 may also provide the volume halving time (VHTime) or response velocity (RV) in responding lesions, with values in shrinking tumors given as VDN ($-\Delta n$) per unit time (TI, as selected time interval).

For so-called individualized, personalized response parameters, such as in Gastrointestinal Stromal Tumors (GIST) where PET scans can show dramatic loss of metabolic activity yet the (maximal) diameters may be greater, the device 100 may be helpful to quantitate PR (partial response) and progression. One uses volumes and VDN (n) values to subtract metabolically inactive volume(s) from maximal image or clinical (palpable) volumes, with the remaining volume then calculated and expressible as truer smaller volume and lower VDN (n) value.

Thus with the device 100 of FIG. 1A, the spherical volume of a lesion is based on a single diameter (radius*2) measurement, and the number of times the volume has doubled in size since being one cubic centimeter (1 cm^3 or 1 cc). Data on the device 100 is normalized to a reference volume of 1 cc, being that, for example, cubic centimeter of tumor may contain up to 1 billion cancer cells. A use of volume doubling VDN (n) for counting tumor growth, 30 doublings, or $2^{30}$ times one cell, results in a volume of 1 cc, when the volume of a single cell is placed at 931 fL (femto-Liters, e.g., a microncube). This is about 10 times the size of an erythrocyte (human red blood cell) and is comparable to many dividing (nucleated) cells such as lymphocytes. Thus, the volume doubling number VDN (n) is set as VDN (n) of 30 for 1 cc; the radius of which is 0.62 cm, with unit increases in VDN (n) obtained by multiplying the radius (or diameter) by 1.26 (the cube root of 2). The device 100 allows one to find the volume and the VDN (n), from a single radius (diameter) measurement.

The smallest radiographic or clinically observed lesion historically accepted as a suitable parameter of response to treatment, is 1 cm diameter, and is equal to a VDN (n) of 29 with a diameter of 0.985 cm, with a radius of 0.492 cm. With the device 100, the arc segments in the first zone enables an instant conversion of diameters (radii) of lesions into VDN (n) values. A measurement of radiographic lesions based on peripheral arc segments may be superior to maximal diameter(s) alone.

When determining the status of the clinical lesion, the size of the clinical lesion may be compared against a lookup chart such as Chart 1, below

CHART 1

| | VDN (n) | | | | |
|---|---|---|---|---|---|
| | 30 | 30.3 | 30.5 | 30.8 | 31 |
| Volume cc | 1.00 | 1.23 | 1.41 | 1.74 | 2.00 |
| Area cm^2 | 1.21 | 1.39 | 1.52 | 1.75 | 1.92 |
| Radius cm | 0.62 | 0.66 | 0.70 | 0.75 | 0.78 |
| RECIST | — | SD | SD | Prog | Prog |
| WHO | — | SD | Prog | Prog | Prog |
| Cheson | — | SD | SD | SD | Prog |

Chart 1 shows a grid in which a header (left) column identifies a volume doubling number VDN (n) relative to a predetermined cell size (e.g. 1 cell), lesion measured volume (in cubic centimeters), lesion measured area (in square centimeters), and lesion measured radius (in centimeters). The header column identifies RECIST, the WHO (World Heath Organization) classification and the Cheson criteria for tumor assessment. RECIST (Response Evaluation Criteria In Solid Tumors) is a set of published rules that define when cancer patients improve ("respond"), stay the same ("stable") or worsen ("progression") during treatments. The data columns, on the right of the header column, list different volume doublings VDN (n) of a tumor based on the measured volume, area and/or radius. The listed volume doubling numbers VDN (n) are between 30 and 31 based on a measured volume of between 1 and 2 cc, a measured area of 1.21 to 1.92 cm^2 and a measured radius of 0.62 to 0.78 cm. These values are related by the typical mathematical correlations between a radius, circle and sphere.

Under the RECIST, WHO and Cheson, a tumor having a volume doubling number VDN (n) of 30.3 relative to a predetermined reference tumor size is stable. When the volume doubling number VDN (n) is 30.5, the WHO criteria is the only one of the three criteria that lists the tumor as progressive. When the volume doubling number VDN (n) is 30.8, the Cheson criteria is the only one of the three criteria that lists the tumor as stable. When the volume doubling number VDN (n) is 31, all three criteria list the tumor as being progressive. Accordingly, the measured VDN (n) may be compared against Chart 1, disclosed above to determine if the tumor is stable or progressing.

Figure 1B:
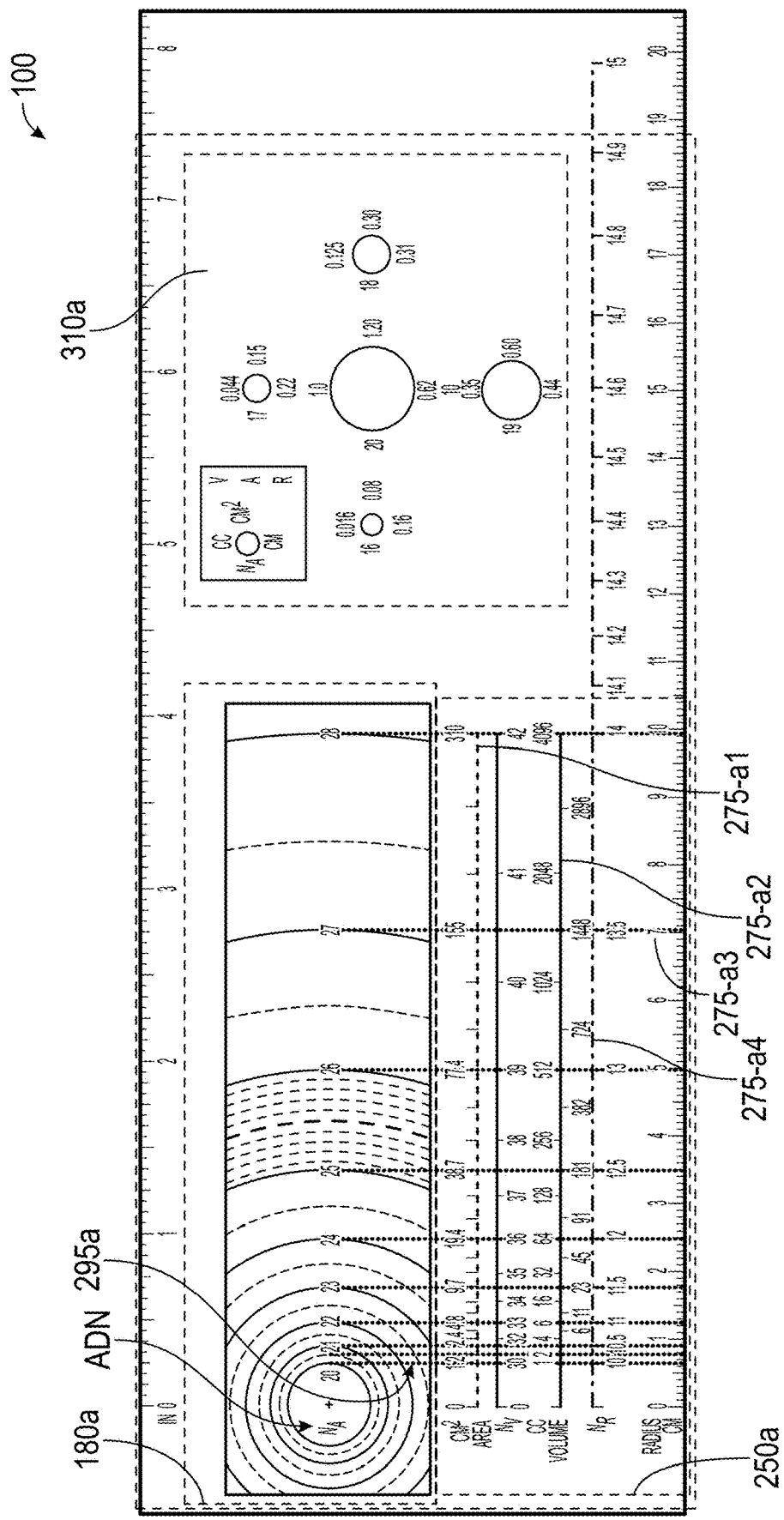
FIG. 1B is another embodiment of the device of FIG. 1A.

Turning to FIG. 1B, an alternative of the device 100 to the embodiment of FIG. 1A is shown. Aspects of FIG. 1B that differ from those in FIG. 1A are identified, however the embodiments are otherwise the same. The first zone 180A may be configured to show ADN (na), from 20-28, rather than VDN. In the second zone 250a, the first (closest) graduated line gauge 275a-1 represents the tumor area, which in this embodiment only shows the area and not the ADN being that the ADN is in the first zone 180A. The second (next closest) graduated line gauge 275a-2 represents the tumor volume and also lists VDN (n) from 30-42. The third and fourth graduated line gauges 275a-3, 275-4 are the same as that in FIG. 1A. The third zone 310A has fewer full circles, i.e., there are five circles in the third zone in FIG. 1B while there are seven in FIG. 1A but that is not intended on limiting the scope of the embodiments. As can be seen, either of the embodiments of FIGS. 1A and 1B may be utilized to identify the info required for Chart 1, to thereby identify a status of a tumor, as well as the volume halving time (VHTime), or response velocity (RV). The RV represents a differential of size (e.g., volumetric) over time, e.g., dV/dt, where V represents volume as a function of time, where time is measured in days, weeks or months, as non-limiting examples. RV, as can be appreciated, has units of cc/(unit of time measurement). Also, as can be appreciated, in the embodiment of FIG. 1B, the VDN (n) parameters of the first zone in FIG. 1A are swapped with the ADN (na), but the range of these parameters remains the same in these embodiments, e.g., in the first and second zones.

The device 100 of FIG. 1B enables use of the radius (diameter/2) of a lesion to be converted into an area doubling number ADN (na) with reference to the maximal cross-section of the corresponding spherical volume VDN (n). Thus, the ADN (na) of 20 corresponds with a radius of 0.62 cm, with area of 1.2 cm^2 corresponds to the VDN (n) of 30 volume of 1.0 cc shown with the drop line 295a.

There are at least two reasons for having separate doubling rulers for volume and area. First, an argument could be supposed that both WHO and Cheson criteria using products of perpendicular diameters are areas as heuristic surrogates of tumor size without necessarily attempting tumor volume estimates, such as in single plane lesions on radiographs and on physical exam. Second, a need for a separate ADN identifier is in dermatology, when the depth of lesions can be only poorly estimated or supposed, and a need for following how quickly the area is doubling in size, using arc and circular peripheral margins. As in pigmented lesions' growth indicative by an ADN (+Δna) and for shrinkage indicative by an ADN (−Δna).

The third zone 310a shows the areas from 0.08 cm^2 with radius of 0.16 cm (1.6 mm) and ADN (na) of 16 doubling up the size of ADN (na) of 20, which is the reference size of the center circle in the first zone, e.g., having an ADN (na) of 20. As in the device of FIG. 1A, separating out the smallest, central circle avoids the issues with line arc crowding as well as the illusion of the centermost doubling circle's illusion of being too close to the next largest circle. The device of FIG. 1B can accommodate situations where purely initial growth of a lesion, such a superficial spreading melanoma, with only a planar presentation, in growth becomes nodular and more spherical by exam or by dermoscopy. The ADR then can be applied for both 2D and 3D data, with both slower rising area ADN (na) and faster-rising volume numbers ADN (+Δna) used for growth (since the VDN is 3/2 times faster per unit volume than the ADN).

Figure 1C:
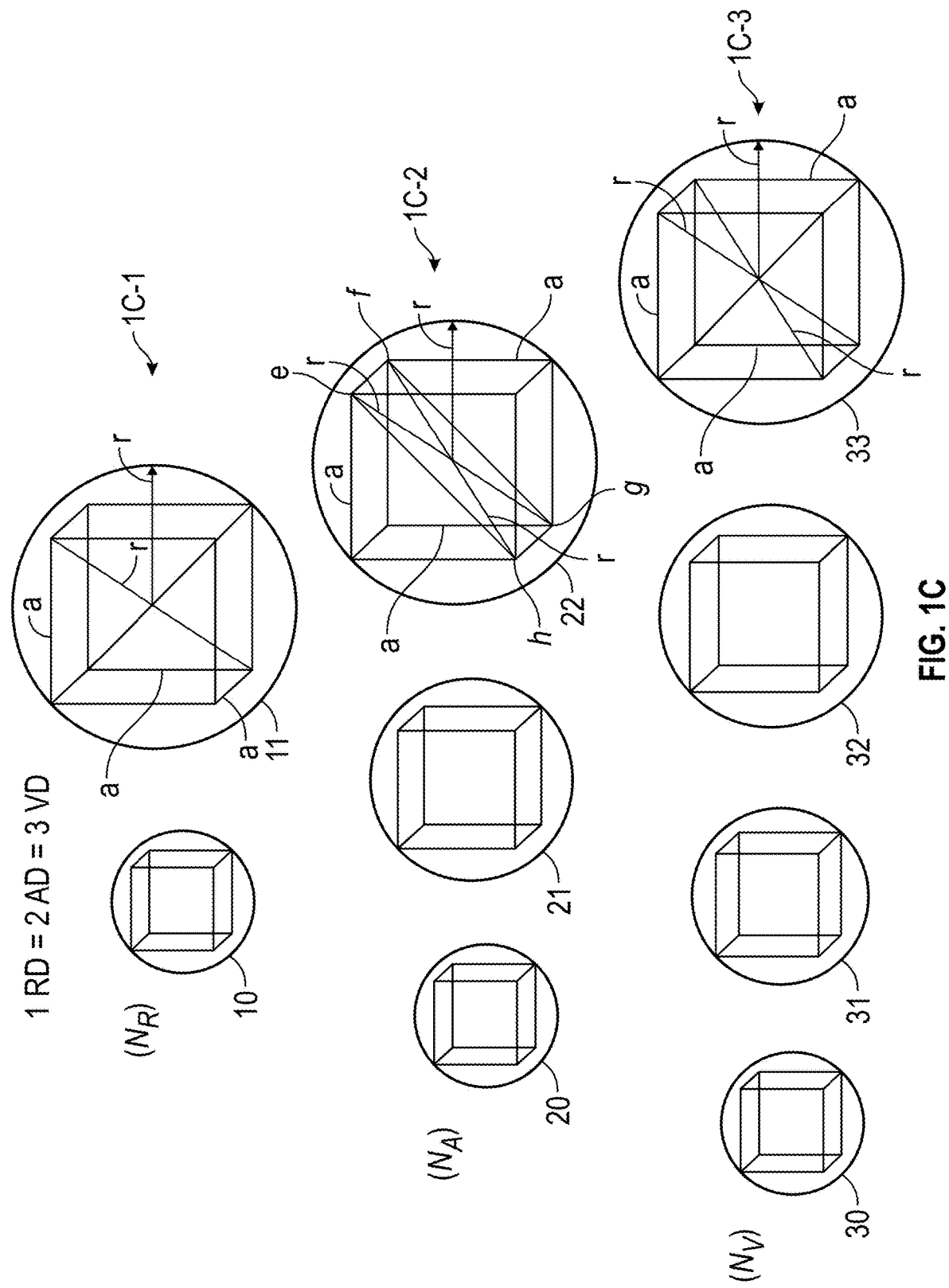
FIG. 1C provides a geometrical argument that supports a position that that one doubling of radius is identical in circle diameters to 2 doublings of area and 3 doublings of volume.

FIG. 1C, provides a geometrical argument that supports a position that that one doubling of radius is identical in circle diameters to 2 doublings of area and 3 doublings of volume. The top row 1C-1 of FIG. 1C shows circles corresponding to RDN (nr), with a RDN range of 10 to 11. The middle row 1C-2 shows circles corresponding to ADN (na), with an ADN range of 20 to 22. The bottom row 1C-3 shows circles corresponding to VDN (n), with a VDN range of 30 to 33. What is shown is the standard way of demonstrating a cube (representing a mass) inscribed in a sphere, with two vertices in contact with spheres represented by circles. All vertices are in contact with the sphere, that cannot be well shown using line drawings. But two observations are made. First, as the "mass" (the cube) retains the same ratios of x, y, and z-axes, and keeps the same orientation in the plane of radiographic imaging, the doubling changes in the mass will be in same proportion to changes in the radius (diameter) of the sphere. Second, any constant plane or sub-section, such as the e-f-g-h surface—a plane of the internal prism—seen at an oblique angle—remaining at the same orientation of observation within the sphere will also preserve the doubling relationship of 3 VD=2 AD=1 RD of the inscribing sphere.

Figure 2A:
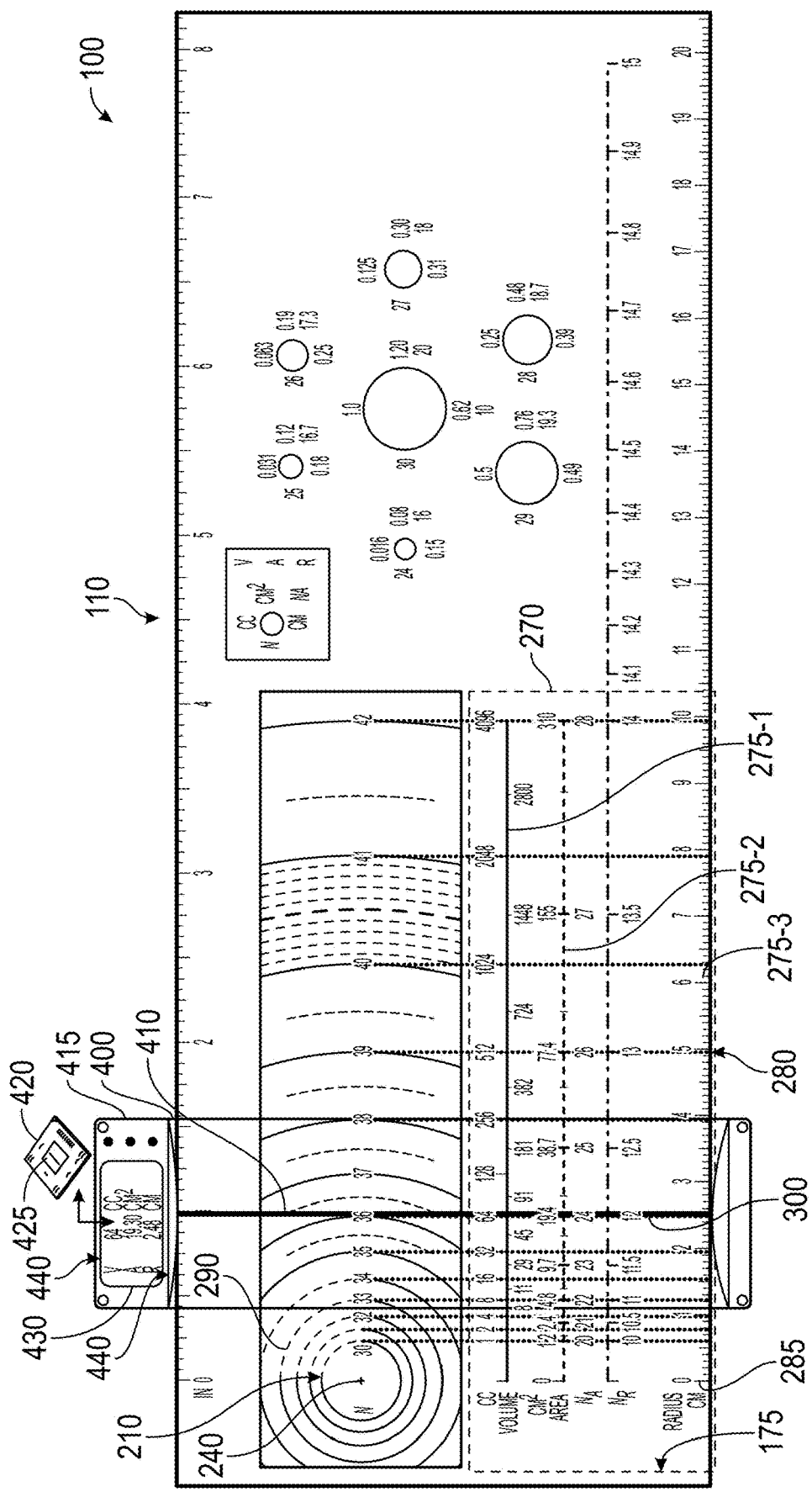
FIG. 2A is a device for evaluating a tumor stability, wherein the device is a slide ruler according to an embodiment.

Turning to FIG. 2A, another embodiment of the device 100 is shown. Aspects of the embodiment in FIG. 2A differ from the embodiment shown in FIG. 1A to the extent identified in this disclosure. Aspects not expressly identified as differing from the embodiment in FIG. 1A should be considered the same as that embodiment.

In the embodiment of FIG. 2A, a slider 400 may be configured to slide longitudinally along the device 100. The slider 400 defines a laterally extending marker 410, which may function similarly to the drop lines 295 (FIG. 1A). A size measurement of the clinical lesion that is centered on the concentric center 240 is obtained by positioning the device 100 against a lesion so that the lesion is at the concentric center 240 in the first zone. Then the slider 400 may be moved so that the marker 410 laterally extends as a tangent from the one of the first zone arcs 210, such as ac 290, correlating a size of the clinical lesion. The marker 410 thereby extends to a respective one 300 of the second zone size markers 280.

An electronics housing 415 may be connected to the slider 400. An electronics controller 420 may be disposed within the slider housing 415. A slider display 430 on the slider housing 415 may be operationally connected to the electronics controller 420. It is to be appreciated that another display connected via suitable wireless or wired connections to the device may be suitable alternatives. A motion sensor 440 or other suitable sensor may be operationally connected to the electronics controller 420. The motion sensor 440 is configured to sense an extent of longitudinal movement of the slider 400 along the device 100. That is, the motion sensor 400 senses movement between the zero-marker 285 of the second zone size markers 280 and the second zone second end 270. The motion sensor 440 may be an electro-mechanical device, such as a roller operationally connected to the electronics controller 420 and configured to roll on the planar surface 110 or edge thereof as the slider 400 moves.

Thus, the longitudinal positioning of the slider 400 is proportional to a size of the clinical lesion being measured.

The electronics controller 420, responsive to the slider 400 being moved, is configured to control the slider display 430 to provide display indicia 440. The display indicia 440 is indicative of the one or more of radius R, area A, volume V, the volume doubling number VDN (n) and area doubling number ADN (na). The electronics controller 420 may include memory 425 that stores a lookup table corresponding to Chart 1, so that a stability indicator may also be displayed. Though the data zones 175 are shown as those corresponding to FIG. 1A, the data zones could correspond to those in FIG. 1B.

The device 100 of FIG. 2A may be configured to identify an SDN for an elliptical lesion. For example the relationship identified in FIG. 2B may be programmed into the controller 420, e.g., via a lookup chart. When measuring a size of a lesion, the controller via may ask the display whether the lesion is elliptical in shape. If so, the controller may instruct the user to measure a first vector (e.g., one-dimension) corresponding to the major axis of the ellipse, which it will store as the length. Then the controller may instruct the user to measure a second vector corresponding to the minor axis of the ellipse, which it will store as the width. The controller may then calculate the length to width (L/W) ratio.

Figure 2B:
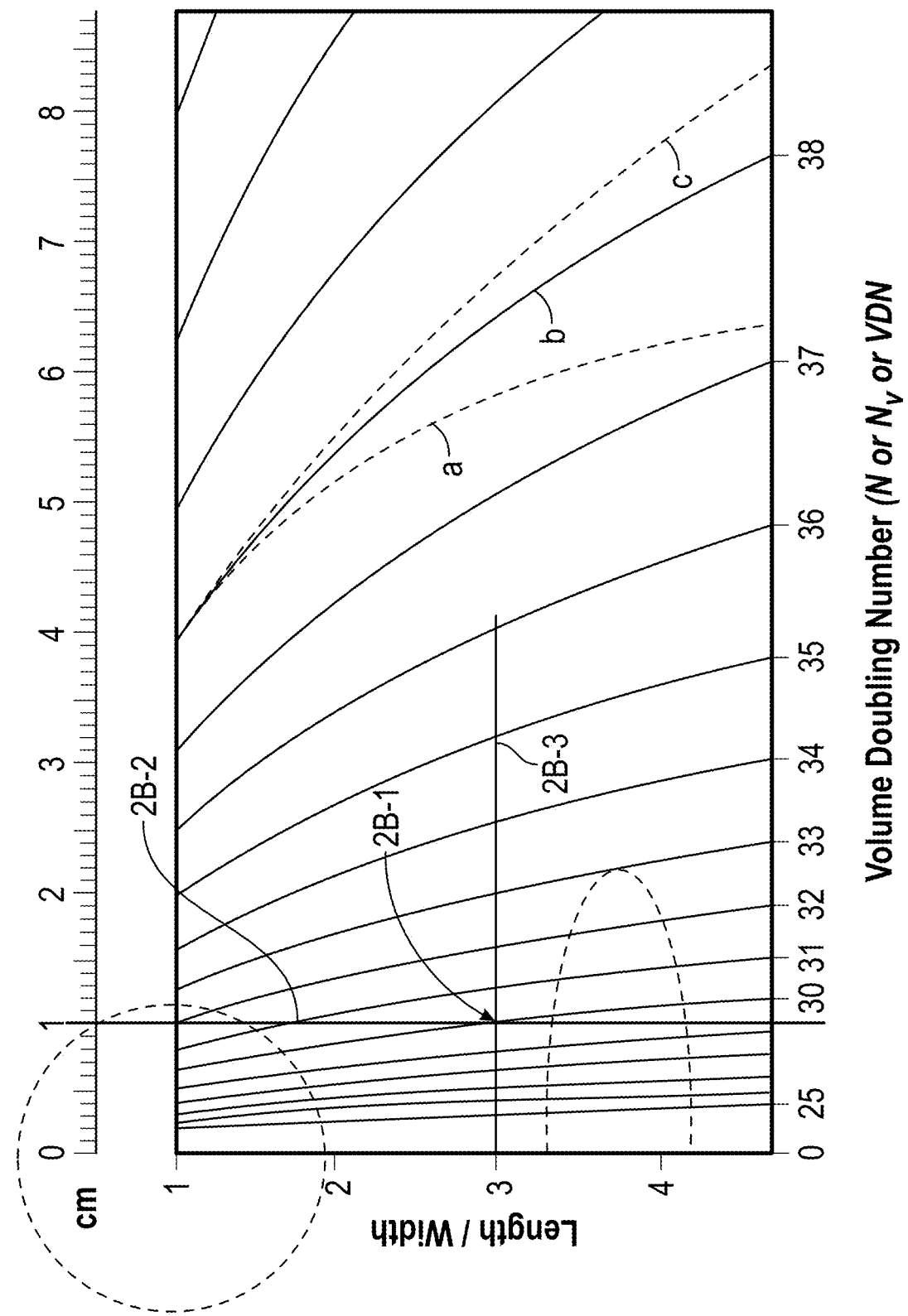
FIG. 2B is a volume doubling number correlation graph for an elliptical lesion.

FIG. 2B is a volumetric conversion chart for an elliptical lesion. Based on the measured length and L/W ratio, the controller may identify the VDN (n). The horizontal axis in FIG. 2B provides for measuring the lesion in cm, the vertical axis in FIG. 2B provides for identifying the L/W ratio. Individual VDN (n) curves are graphed on the chart ranging from a VDN (n) of 25 to a VDN (n) of 38. For example, if the L/W is 3 and the length is 1 cm, then the VDN (n) is 30, based on the intersect identified as 2B-1 with lines 2B-2, 2B-3. The volume or area can then be obtained by via the information provided in the zones 175, which are also programed into the controller. In FIG. 2B, reference line a is for calculating VDN (n) based on $[(L+W)/2]^3$, which may be considered an average diameter method. Reference line b is for calculating VDN (n) based on $[(L*W)(L+W)/2]$. Reference line c is for calculating VDN (n) from the geometric mean of L and W: [sq root of $(L*W)][(L*W)]$. The value of b splits the difference for all three options by weighting L and W equally. In some embodiments the controller may ask the user via the display which of these options for calculating volume is preferred for a VDN (n) determination. It is to be appreciated that values of a-c may be achieved for each VDN (n) curve in the chart.

In addition, for a given organ, there may be more than one lesion. Clinically a single size doubling number for a set of lesions on an organ can be obtained to determine if there is stability, progression, etc. for the lesion. This would be obtain by summing a volume of the lesions using any of the embodiments identified herein, and for example using the volume line gauge in the second zone to find the VDN (n) in the first zone. Thus, the controller in the embodiment in FIG. 2 may ask via the display whether any additional lesions should be measured. If multiple lesions are required to be measured, the volume of each is calculated, stored in memory as required, and summed. Then the VDN (n), and resulting evaluation, is obtained from the summed volume.

Figure 3:
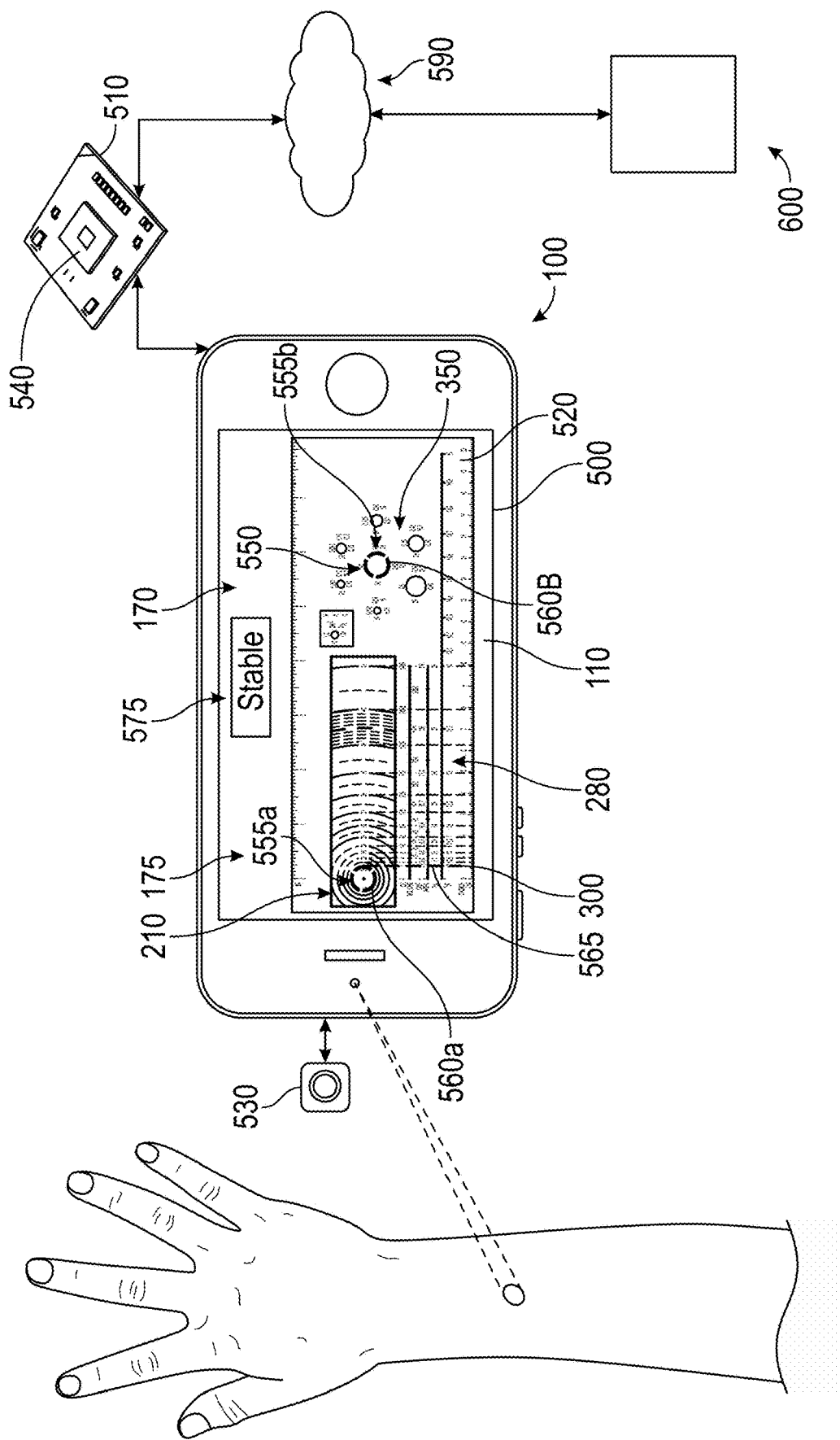
FIG. 3 is a device for evaluating a tumor stability, wherein the device is a smart device according to an embodiment.

Turning to FIG. 3, a further embodiment of the device 100 is shown. Aspects of the device 100 that are shown as being the same as aspects in any one of the previous FIGS. are the same as previously described unless otherwise indicated.

The device 100 includes device housing 500. The device 100 is shown as a smart device, such as a mobile phone. A device controller 510 may be within the housing 500. A device display 520 may be defined on the device housing 500. The device display 520 may be operationally connected to the device controller 510. The device display 520 may define the planar surface 110. The device controller 510 may be configured to display the data portion 170 on the device display 520. In addition, the data zones 175 of the data portion 170 may include a fourth zone 575 for identifying a stability status of the lesion. It is to be appreciated that another display connected via suitable wireless or wired connections to the device may be suitable alternatives. The device 100 may include a camera 530 or similar sensor, utilized as indicated below.

The device 100, via the device controller 510, may be configured to execute software stored on memory 540 to thereby execute a process for evaluating a clinical lesion. Turning to FIGS. 3-4, as shown in block 1000, the process includes displaying the data portion 170, e.g., with one or more data zones, on the device display 520. As shown in block 1010, the process includes capturing, via the camera 530, a lesion image of the clinical lesion, or alternatively from direct VDR/ADR readings or from the slider sensor data of 400/430. As shown in block 1020, the method includes determining, from the lesion image, a size of the clinical lesion. As shown in block 1030, the method includes applying size indicia 550 indicative of an evaluation of the lesion to one or more of the data zones 175. The size indica 550 may be indicative of a size of the clinical lesion, which may be the VDN (n), the ADN (na), the RDN (nr), the radius, area and volume. Though the data zones 175 are shown as those corresponding to FIG. 1A, the data zones could correspond to those in FIG. 1B.

Turning to FIGS. 3-5, and as shown block 1040, when applying the size indicia 550 (block 1030), the device 100 may be configured for layering a schematic representation generally referenced as 555 of the clinical lesion over one or more of: one 560a of the first zone arcs 210 correspond to the size of the clinical lesion; and one 560b of the third zone circles 350 corresponding to the size of the clinical lesion that are smaller than the first zone arcx. The device 100 renders a determination about which circle to associate with the lesion based on the size of the lesion.

As shown in block 1050, when applying the size indicia 550, the device 100 may be configured for layering a tangent 565 (similar to the drop line 295) from the one 560b of the first zone arcs 210 to a respective one 300 of the second zone size markers 280 corresponding to the size of the clinical lesion. This enables a user to identify one or more of a volume, area and radius, radius doubling, area doubling and volume doubling number of the lesion.

Turning to FIGS. 3, 4 and 6, and as shown in block 1060, when providing the size indicia 550 (block 1030), the device 100 may be configured for evaluating the clinical lesion from the size of the clinical lesion. As shown in block 1070, the device 100 may be configured for providing status indicia in the fourth zone 575. The status indica in the fourth zone 575 identifies that the clinical lesion is stable or progressing.

Turning to FIGS. 6 and 7, when evaluating the clinical lesion (block 1060), the device 100, via the device controller 510, may be configured for comparing the size of the clinical lesion against a lookup chart 580, e.g., Chart 1, as shown in block 1080. That is, Chart 1, above, may be programmed into the device 100 and automatically utilized by the device 100 upon determining a VDN (n) of the tumor to determine of the tumor is stable or progressing.

Turning to FIGS. 6 and 8, when evaluating the clinical lesion (block 1060), the device 100 may be configured for comparing the size of the clinical lesion with a previously observed size of the clinical lesion as shown in block 1090. The previously observed size may be stored as data on the device 100 or retrievable by the device 100, via a network 590, from a cloud service 600. As shown in block 1100, from the comparing, the device 100 may be configured for rendering a lesion change determination. The change determination includes one or more of growth, shrinkage, growth rate and shrinkage rate of one or more of radius R, area A, volume V, and size doubling number (SDN) of the clinical lesion. The lesion change determination may be represented as its volume doubling time (VDTime), volume halving time (VHTime) or regression velocity (RV) may be obtained, as indicated above. According to this embodiment the status indicia in the fourth zone 575 may also be indicative of the rendered lesion change determination.

Turning to FIGS. 4 and 9, when determining the size of the clinical lesion (block 1020) at block 1110, the device 100 may be configured for inquiring via the display whether a single or multiple lesions (e.g., on an organ) are being considered for the evaluation. If multiple lesions are considered, at block 1120 the device 100 may configured for successively determining a size for each lesion, storing the determined sizes, and determining a total size (e.g., a volume) for the multiple lesions. The SDN (e.g., a VDN (n)) and evaluation may then be determined for the multiple lesions based on the total size. That is the device 100 may evaluate the multiple lesions as the clinical lesion for purposes of identifying the SDN. Prompting for whether there are multiple lesions, and thereafter prompting for a next lesion of the multiple lesions, may be via the fourth data zone 575.

Turning to FIGS. 4 and 10, when determining when determining the size of the clinical lesion (block 1020) at block 1130, the device 100 may be configured for determining that the lesion is elliptically shaped. Then at block 1140, the device 100 may be configured for determining a length and width, and determining the L/W ratio of the lesion per the discussion of FIG. 2B above. The device 100 may have stored in memory the VDN (n) correlation table for the elliptical lesion. At block 1150, the device 100 may be configured for determining a SDN, e.g., the VDN (n), of the lesion with reference to the determined length and width, and the determined L/W ratio, and further reference to the VDN correlation information, e.g., the table of FIG. 2B stored in memory or available via a wireless communication over a network, e.g., with a cloud service. As indicated, the table of FIG. 2B is a function of lesion length and the lesion L/W ratio. In some embodiments the controller may ask the user via the display which of the options for calculating volume identified with graph lines a, b and c are preferred for a VDN (n) determination. With the device 100 of FIG. 3 once an image of a lesion is captured, a diameter of the lesion may be determined as twice the radius. A radii may be determined as the distance between a centroid of the arc in which the lesion is placed in the first zone to an arc edge of the arc. For an arc that traces a full circle, such VDN (n) of 30 in the first and third zones, the diameter may be determined either by a distance between opposing arc edges, or as a product of perpendicular diameters, e.g., an arc edge to an arc edge.

Figure 11:
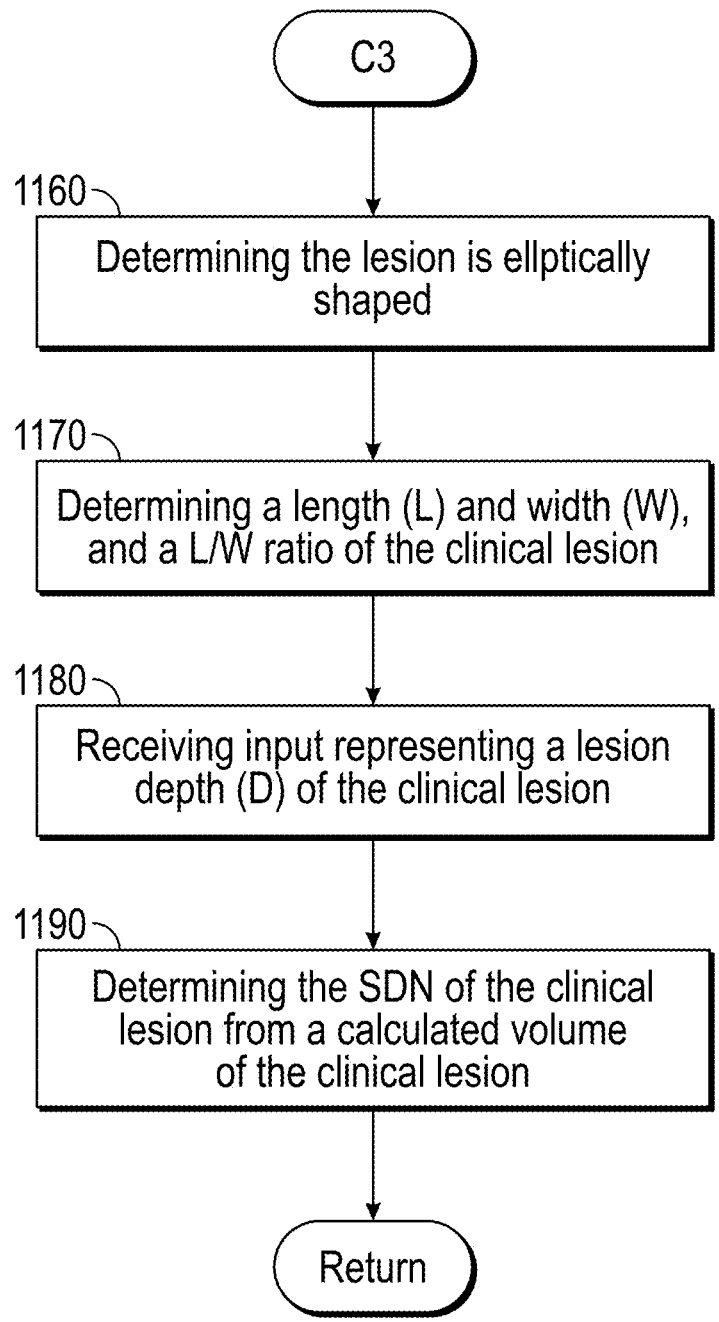

Turning to FIGS. 4 and 11, when determining the size of the clinical lesion (block 1020) at block 1160, the device 100 is configured for determining that the lesion is elliptically shaped. At block 1170, the device 100 is configured for determining a length (L) and width (W) of the clinical lesion, e.g., using the camera of the device 100. At block 1180, the device 100 is configured for receiving input representing a lesion depth (D) of the clinical lesion, e.g., following prompting via the fourth data zone 575. At block 1190, the device 100 is configured for determining the SDN of the clinical lesion from a calculated volume of the clinical lesion, where the calculated volume is based on L, W and D. The SDN may be determined from the volume information as indicated above, e.g., with the correlations for FIGS. 1A and 1B stored in memory or accessible over wireless connection to a web server, such as a cloud service, to name a few non-limiting alternatives. In this embodiment, the correlations in FIG. 2B may be unnecessary as the L/W ratio is not relied upon.

It should be appreciated that the image of a lesion may be obtained in the plane of the lesion. In the case of images obtained from other scans or photographs, calibration may be required through the use of other measurement data and/or conversion factors.

As can be appreciated, the RDN (nr) provides a magnification factor (MF) that may be commonly used in optics, microscopy, telescopes, and gunsights. A MF value of X is a Radius (R)*X. Thus a MF where X=10 with the R appearing 10 times bigger (longer, wider) is given by $2^{(\Delta nR)}$. In terms of logs: log 10=Δnr*log 2, and Δnr is 0/0.30103 or 3.32 radius doublings. Further, Log(MF)=Δnr*log 2, or stated in reverse, Δnr=log(MF)/log 2 or log(MF)/0.30103. By utilizing RDN, for example, with respect to optics, with a 32×MF, $2^{(\Delta nr)}$ with Δnr=5, one can find how many area doublings (AD) of (2*5=10 AD) and volume doublings (VD) of (3*5=15 VD) that may result from the radius MF. Thus, the embodiment of FIG. 3, for example, with the ability to pan and zoom via a touch sensitive display on a smart device, may accommodate a large or small number for interconversion of radius, area, and volume and resulting RDN (na), ADN (na) and VDN (n).

Accordingly, disclosed above is a device 100 for measuring and deducing a volume, area, and radius doubling of clinical and radiographic tumor parameters of neoplastic disease, and categorization of response to treatment, progression, or stable disease. Whether one is using WHO (World Health Organization), RECIST (Response Evaluation Criteria in Solid Tumors), or Cheson criteria, or personalized response criteria (as in GIST disease). With the VDN (n), and ADN (na), for increased ability in description of disease behavior, including malignant cell count per cubic cm (cm3 or cc) (cell density), volume and area doubling times, and response velocities (RV) (volume and area halving times).

Generally, sensor data identified herein may be obtained and processed separately, or simultaneously and stitched together, or a combination thereof, and may be processed in a raw or complied form. The sensor data may be processed on the sensor (e.g. via edge computing), by controllers identified or implicated herein, on a cloud service, or by a combination of one or more of these computing systems. The senor may communicate the data via wired or wireless transmission lines, applying one or more protocols as indicated below.

Wireless connections may apply protocols that include local area network (LAN, or WLAN for wireless LAN) protocols. LAN protocols include WiFi technology, based on the Section 802.11 standards from the Institute of Electrical and Electronics Engineers (IEEE). Other applicable protocols include Low Power WAN (LPWAN), which is a wireless wide area network (WAN) designed to allow long-range communications at a low bit rates, to enable end devices to operate for extended periods of time (years) using battery power. Long Range WAN (LoRaWAN) is one type of LPWAN maintained by the LoRa Alliance, and is a media access control (MAC) layer protocol for transferring management and application messages between a network server and application server, respectively. LAN and WAN protocols may be generally considered TCP/IP protocols (transmission control protocol/Internet protocol), used to govern the connection of computer systems to the Internet. Wireless connections may also apply protocols that include private area network (PAN) protocols. PAN protocols include, for example, Bluetooth Low Energy (BTLE), which is a wireless technology standard designed and marketed by the Bluetooth Special Interest Group (SIG) for exchanging data over short distances using short-wavelength radio waves. PAN protocols also include Zigbee, a technology based on Section 802.15.4 protocols from the IEEE, representing a suite of high-level communication protocols used to create personal area networks with small, low-power digital radios for low-power low-bandwidth needs. Such protocols also include Z-Wave, which is a wireless communications protocol supported by the Z-Wave Alliance that uses a mesh network, applying low-energy radio waves to communicate between devices such as appliances, allowing for wireless control of the same.

Wireless connections may also include radio-frequency identification (RFID) technology, used for communicating with an integrated chip (IC), e.g., on an RFID smartcard. In addition, Sub-1 Ghz RF equipment operates in the ISM (industrial, scientific and medical) spectrum bands below Sub 1 Ghz—typically in the 769-935 MHz, 315 Mhz and the 468 Mhz frequency range. This spectrum band below 1 Ghz is particularly useful for RF IOT (internet of things) applications. The Internet of things (IoT) describes the network of physical objects-"things"—that are embedded with sensors, software, and other technologies for the purpose of connecting and exchanging data with other devices and systems over the Internet. Other LPWAN-IOT technologies include narrowband internet of things (NB-IOT) and Category M1 internet of things (Cat M1-IOT). Wireless communications for the disclosed systems may include cellular, e.g. 2G/3G/4G (etc.). Other wireless platforms based on RFID technologies include Near-Field-Communication (NFC), which is a set of communication protocols for low-speed communications, e.g., to exchange date between electronic devices over a short distance. NFC standards are defined by the ISO/IEC (defined below), the NFC Forum and the GSMA (Global System for Mobile Communications) group. The above is not intended on limiting the scope of applicable wireless technologies.

Wired connections may include connections (cables/interfaces) under RS (recommended standard)-422, also known as the TIA/EIA-422, which is a technical standard supported by the Telecommunications Industry Association (TIA) and which originated by the Electronic Industries Alliance (EIA) that specifies electrical characteristics of a digital signaling circuit. Wired connections may also include (cables/interfaces) under the RS-232 standard for serial communication transmission of data, which formally defines signals connecting between a DTE (data terminal equipment) such as a computer terminal, and a DCE (data circuit-terminating equipment or data communication equipment), such as a modem. Wired connections may also include connections (cables/interfaces) under the Modbus serial communications protocol, managed by the Modbus Organization. Modbus is a master/slave protocol designed for use with its programmable logic controllers (PLCs) and which is a commonly available means of connecting industrial electronic devices. Wireless connections may also include connectors (cables/interfaces) under the PROFibus (Process Field Bus) standard managed by PROFIBUS & PROFINET International (PI). PROFibus which is a standard for fieldbus communication in automation technology, openly published as part of IEC (International Electrotechnical Commission) 61158. Wired communications may also be over a Controller Area Network (CAN) bus. A CAN is a vehicle bus standard that allow microcontrollers and devices to communicate with each other in applications without a host computer. CAN is a message-based protocol released by the International Organization for Standards (ISO). The above is not intended on limiting the scope of applicable wired technologies.

When data is transmitted over a network between end processors as identified herein, the data may be transmitted in raw form or may be processed in whole or part at any one of the end processors or an intermediate processor, e.g., at a cloud service (e.g. where at least a portion of the transmission path is wireless) or other processor. The data may be parsed at any one of the processors, partially or completely processed or complied, and may then be stitched together or maintained as separate packets of information. Each processor or controller identified herein may be, but is not limited to, a single-processor or multi-processor system of any of a wide array of possible architectures, including field programmable gate array (FPGA), central processing unit (CPU), application specific integrated circuits (ASIC), digital signal processor (DSP) or graphics processing unit (GPU) hardware arranged homogenously or heterogeneously. The memory identified herein may be but is not limited to a random access memory (RAM), read only memory (ROM), or other electronic, optical, magnetic or any other computer readable medium. Embodiments can be in the form of processor-implemented processes and devices for practicing those processes, such as processor. Embodiments can also be in the form of computer code based modules, e.g., computer program code (e.g., computer program product) containing instructions embodied in tangible media (e.g., non-transitory computer readable medium), such as floppy diskettes, CD ROMs, hard drives, on processor registers as firmware, or any other non-transitory computer readable medium, wherein, when the computer program code is loaded into and executed by a computer, the computer becomes a device for practicing the embodiments. Embodiments can also be in the form of computer program code, for example, whether stored in a storage medium, loaded into and/or executed by a computer, or transmitted over some transmission medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an device for practicing the exemplary embodiments. When implemented on a general-purpose microprocessor, the computer program code segments configure the microprocessor to create specific logic circuits.

Various aspects of the embodiments may be summarized as follows:

According to a first aspect of the embodiments, a device 100 for identifying a size doubling number (SDN) of a clinical lesion relative to a predetermined size of the clinical lesion, the device 100 including: a planar surface 110 including a first planar surface end 120, the planar surface 130 extending longitudinally aft from the first planar surface end 120 to a second planar surface end 140; the planar surface 130 defining a data portion first end 160 that is adjacent the first planar surface end 120, and a data portion 170 extending longitudinally aft from the data portion first end 160 to a data portion second end 174, wherein the data portion 170 includes data zones 175, including: a first zone 180 defining a first zone first end 190 that is adjacent the data portion first end 160, the first zone 180 extending longitudinally aft from the first zone first end 190 to a first zone second end 205, wherein: the first zone 180 defines first zone arcs 210, the first zone arcs 210 being distributed in a concentric configuration, the first zone arcs 210 defining first mutually unique radiuses R1, ranging from a first minimum radius R1min of a first zone first arc 220 to a first maximum radius R1max of a first zone last circle 230, and wherein a concentric center 240 of the first zone arcs 210 is adjacent the first zone first end 190; the first zone arcs 210 are successively larger from each other by a predetermined multiplication factor; the first zone 180 includes first zone size markers 245, respectively positioned adjacent ones of the first zone arcs 210, and the first zone size markers 245 respectively identify the size doubling number (SDN) of the clinical lesion having a size that corresponds to a respective one of the first zone arcs 210.

According to a second aspect of the embodiments, in addition to one or more of the above aspects of the device, the data zones 175 include: a second zone 250 that is laterally adjacent the first zone 180, the second zone 250 defining a second zone first end 260 that is longitudinally aligned with the first zone 180, the second zone 250 extending longitudinally aft from the second zone first end 260 to a second zone second end 270, wherein: the second zone 250 defines a graduated line gauge 275 and defines second zone size markers 280, wherein the second zone size markers 280 identify one or more of radius R, area A, volume V, and the SDN of the clinical lesion.

According to a third aspect of the embodiments, in addition to one or more of the above aspects of the device, the first zone arcs 210 are laterally aligned and longitudinally spaced apart from each other within the first zone 180, between the concentric center 240 and the first zone second end 205; and the first zone first arc 220 represents $2^{n1}$ volume doublings relative to a single tumor cell of the clinical lesion, and the first zone last arc 230 represents $2^{m1}$ volume doublings relative to the single tumor cell, where m1=n1+c1, wherein c is the number of circles in the first zone arcs 210, and wherein n1=30, and c1=10 or greater.

According to a fourth aspect of the embodiments, in addition to one or more of the above aspects of the device, the device includes a third zone 310 defining a third zone first end 320 adjacent to the first zone second end 205, and the third zone extending longitudinally aft from the third zone first end 320 to a third zone second end 340, wherein: the third zone 310 defines third zone circles 350 and includes third zone size markers 360, the third zone circles 350 being distributed in a non-overlapping configuration and defining second mutually unique radiuses R2 ranging from a second minimum radius R2 min of a third zone first circle 370 to a second maximum radius R2max of a third zone last circle 380; each successively larger circle in the third zone circles 350 is larger than each successively smaller circle in the third zone circles 350 by the first multiplication factor; the first minimum radius R1min of the first zone arcs 210 is the same as or greater than the second maximum radius R2max of the third zone circles 350; the third zone size markers 360 identify one or more of radius R, area A, volume V and the size doubling number (SDN) of the clinical lesion having a size that corresponds to a respective one of the third zone circles 350.

According to a fifth aspect of the embodiments, in addition to one or more of the above aspects of the device, the third zone first circle 370 represents $2^{n2}$ volume doublings of the single tumor cell relative to the clinical lesion, and the third zone last circle 380 represents $2^{m2}$ volume doublings relative to the single tumor cell, where m2=n2+c2, wherein c2 is the number of circles in the third zone circles 350, and wherein n2=24, and c2=7 or more.

According to a sixth aspect of the embodiments, in addition to one or more of the above aspects of the device, the device 100 defines a ruler that is at least partially transparent, wherein the planar surface 110 is approximately rectangular and is smaller in a lateral direction L1 than a longitudinal direction L2.

According to a seventh aspect of the embodiments, in addition to one or more of the above aspects of the device, the device includes a slider 400 configured to slide longitudinally along the planar surface 110, the slider 400 defining a laterally extending marker 410, wherein a size measurement of the clinical lesion is obtained by positioning the laterally extending marker 410 so that it laterally extends as a tangent from one of the first zone arcs 210 corresponding to a size of the clinical lesion to a respective one 300 of the second zone size markers 280.

According to an eighth aspect of the embodiments, in addition to one or more of the above aspects of the device, the device includes an electronics housing 415 connected to the slider 400; an electronics controller 420 within the slider housing 415; a slider display 430 on the slider housing 415 that is operationally connected to the electronics controller 420; and a motion sensor 440 operationally connected to the electronics controller 420 and configured to sense an extent of longitudinal movement along the device 100, wherein the longitudinal movement is proportional to a size of the clinical lesion being measured, wherein the electronics controller 420, responsive to the sensing, is configured to control the slider display 430 to provide display indicia 440 indicative of the one or more of radius R, area A and volume V, radius doubling number, area doubling number and volume doubling number of the clinical lesion being measured.

According to a ninth aspect of the embodiments, in addition to one or more of the above aspects of the device, the device includes a device housing 500; a device controller 510 within the device housing 500; a device display 520 defined on the device housing 500, the device display 520 operationally connected to the device controller 510, the device display 520 defining the planar surface 110; wherein the device controller 510 is configured to display the data portion 170 on the device display 520.

According to a tenth aspect of the embodiments, in addition to one or more of the above aspects of the device, the device 100 is a mobile device that includes a camera 530, and wherein the device 100, via the device controller 510, is configured to execute software stored on memory 540, to: display the data portion 170 on the device display 520, capture, via the camera 530, a lesion image of the clinical lesion; determine, from the lesion image, a size of the clinical lesion; and apply size indicia 550 to one or more of the data zones 175, wherein the size doubling indica 550 is indicative of one or more of radius R, area A and volume V, radius doubling number, area doubling number and volume doubling number of the clinical lesion being measured.

According to an eleventh aspect of the embodiments, in addition to one or more of the above aspects of the device, when applying the size indicia 550, the device 100 is configured to layer a schematic representation 555 of the clinical lesion over one or more of: one of the circles 560a in the first zone arcs 210 correspond to the size of the clinical lesion; and another one of the circles 560b in the third zone circles 350 corresponding to the size of the clinical lesion.

According to a twelfth aspect of the embodiments, in addition to one or more of the above aspects of the device, when applying the size indicia 550, the device 100 is configured to: layer a tangent 565 from the one of the circles 560b in the first zone arcs 210 to a respective one 300 of the second zone size markers 280 corresponding to the size of the clinical lesion.

According to a thirteenth aspect of the embodiments, in addition to one or more of the above aspects of the device, the data zones 175 include a fourth zone 575 for identifying a stability status of the lesion, and when providing the size indicia 550, the device 100 is configured to: determine a status of the clinical lesion from the size of the clinical lesion, and provide status indicia in the fourth zone 575.

According to a fourteenth aspect of the embodiments, in addition to one or more of the above aspects of the device, when determining the status of the clinical lesion, the device 100, via the device controller 510, compares the size of the clinical lesion against a lookup chart 580.

According to a fifteenth aspect of the embodiments, in addition to one or more of the above aspects of the device, when determining the status of the clinical lesion, the device 100 is configured to: compare the size of the clinical lesion with a previously observed size of the clinical lesion, wherein the previously observed size is stored as data on the device 100 or retrievable by the device 100, via a network 590, from a cloud service 600, from the comparing, rendering a lesion change determination, wherein the change determination includes one or more of growth, shrinkage, growth rate and shrinkage rate of one or more of radius R, area A, volume V, and size doubling number (SDN) of the clinical lesion; and wherein the status indicia in the fourth zone 575 is indicative of the rendered lesion change determination.

According to a sixteenth aspect of the embodiments, a method is disclosed of evaluating a lesion with a smart device, including: displaying a data portion 170 with one or more data zones on a device display 520 of the smart device; capturing, via the camera 530, a lesion image of the clinical lesion; determining, from the lesion image, a size of the clinical lesion; and applying size indicia 550, indicia to one or more of the data zones 175 indicative of an evaluation of the clinical lesion.

According to a seventeenth aspect of the embodiments, in addition to one or more of the above aspects of the method, the method includes: layering a schematic representation 555 of the clinical lesion over one or more of: one of first zone arcs 210 correspond to the size of the clinical lesion; and one of third zone circles 350 corresponding to the size of the clinical lesion that is smaller than the first zone arcs 210.

According to an eighteenth aspect of the embodiments, in addition to one or more of the above aspects of the method, the method includes: evaluating the clinical lesion from the size of the clinical lesion by: comparing the size of the clinical lesion with a previously observed size of the clinical lesion as shown in block 1090; and rendering a lesion change determination.

According to a nineteenth aspect of the embodiments, in addition to one or more of the above aspects of the method, the method includes: evaluating the clinical lesion from the size of the clinical lesion by: comparing the size of the clinical lesion against a lookup chart 580 accessible by the device, via on-board memory or over a wireless connection.

According to a twentieth aspect of the embodiments, in addition to one or more of the above aspects of the method, determining the size of the clinical lesion includes: inquiring via the display whether a single or multiple lesions are being considered for the evaluation; and successively determining a size for each lesion and determining a total size for the multiple lesions.

According to a twenty first aspect of the embodiments, in addition to one or more of the above aspects of the method, determining the size of the clinical lesion includes: determining that the lesion is elliptically shaped; determining a length (L) and width (W), and a L/W ratio of the clinical lesion; and determining the SDN of the clinical lesion with reference to the determined length and width, and the L/W ratio, and further reference to SDN correlation information, which is a function of at least a lesion length and a lesion L/W ratio.

According to a twenty second aspect of the embodiments, in addition to one or more of the above aspects of the method, determining the size of the clinical lesion includes: determining that the lesion is elliptically shaped; determining a length (L) and width (W) of the clinical lesion; receiving input representing a lesion depth (D) of the clinical lesion; and determining the SDN of the clinical lesion from a calculated volume of the clinical lesion, wherein the calculated volume is based on L, W and D.

According to a twenty third aspect of the embodiments, a device is disclosed for identifying a size doubling number of a lesion, including: a planar surface defining a data portion that includes data zones, including: a first zone that defines first zone arcs distributed in a concentric configuration, the first zone arcs defining first mutually unique radiuses, ranging from a first minimum radius to a first maximum radius; the first zone includes first zone size markers, respectively positioned adjacent ones of the first zone arcs, and the first zone size markers respectively identify the size doubling number of the clinical lesion having a size that corresponds to a respective one of the first zone arcs, the size doubling number being one or more of a volume doubling number, an area doubling number and a radius doubling number.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

While the present disclosure has been described with reference to an exemplary embodiment or embodiments, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the essential scope thereof. Therefore, it is intended that the present disclosure not be limited to the particular embodiment disclosed as the best mode contemplated for carrying out this present disclosure, but that the present disclosure will include all embodiments falling within the scope of the claims.

What is claimed is:

1. A device for identifying a-size doubling numbers (SDNs) of a clinical lesion relative to a predetermined size of the clinical lesion, the device comprising:
a planar surface including a first planar surface end, the planar surface extending longitudinally aft from the first planar surface end to a second planar surface end;
the planar surface defining a data portion first end that is adjacent the first planar surface end, and a data portion extending longitudinally aft from the data portion first end to a data portion second end,
wherein the data portion includes data zones, including:
a first zone defining a first zone first end that is adjacent the data portion first end, the first zone extending longitudinally aft from the first zone first end to a first zone second end,
wherein:
the first zone defines first zone arcs, the first zone arcs being distributed in a concentric configuration,
the first zone arcs defining first mutually unique radiuses R1, ranging from a first minimum radius R1min of a first zone first arc to a first maximum radius R1max of a first zone last circle, and
wherein a concentric center of the first zone arcs is adjacent the first zone first end;
the first zone arcs are successively larger from each other by a predetermined multiplication factor;
the first zone includes first zone size markers, respectively positioned adjacent ones of the first zone arcs, and the first zone size markers respectively identify the size doubling numbers (SDNs) of the clinical lesion having a size that corresponds to a respective one of the first zone arcs,
the first zone arcs are laterally aligned and longitudinally spaced apart from each other within the first zone, between the concentric center and the first zone second end; and
the first zone first arc represents $2^{n1}$ volume doublings relative to a single tumor cell of the clinical lesion, and the first zone last arc represents $2^{m1}$ volume doublings relative to the single tumor cell, where $m1=n1+c1$, wherein c is the number of circles in the first zone arcs, and
wherein $n1=30$, and $c1=10$ or greater; and
the data zones include:
a second zone that is laterally adjacent the first zone, the second zone defining a second zone first end that is longitudinally aligned with the first zone, the second zone extending longitudinally aft from the second zone first end to a second zone second end,
wherein:
the second zone defines a graduated line gauge and defines second zone size markers, wherein the second zone size markers identify one or more of radius R, area A, volume V, and the SDN of the clinical lesion.

2. The device of claim 1, including:
a third zone defining a third zone first end that is adjacent to the first zone second end, and the third zone extending longitudinally aft from the third zone first end to a third zone second end,
wherein:
the third zone defines third zone circles and includes third zone size markers, the third zone circles being distributed in a non-overlapping configuration and defining second mutually unique radiuses R2 ranging from a second minimum radius R2min of a third zone first circle to a second maximum radius R2max of a third zone last circle;
each successively larger circle in the third zone circles is larger than each successively smaller circle in the third zone circles by the first multiplication factor;
the first minimum radius R1min of the first zone arcs is the same as or greater than the second maximum radius R2max of the third zone circles;
the third zone size markers identify one or more of radius R, area A, volume V and the size doubling number of the clinical lesion having a size that corresponds to a respective one of the third zone circles.

3. The device of claim 2, wherein:
wherein the third zone first circle represents $2^{n2}$ volume doublings of the single tumor cell relative to the clinical lesion, and the third zone last circle represents $2^{m2}$ volume doublings relative to the single tumor cell, where $m2=n2+c2$, wherein c2 is the number of circles in the third zone circles, and
wherein $n2=24$, and $c2=7$ or more.

4. The device of claim 1, wherein:
the device defines a ruler that is at least partially transparent, wherein the planar surface is approximately rectangular and is smaller in a lateral direction L1 than a longitudinal direction L2.

5. A device for identifying a-size doubling numbers (SDNs) of a clinical lesion relative to a predetermined size of the clinical lesion, the device comprising:
a planar surface including a first planar surface end, the planar surface extending longitudinally aft from the first planar surface end to a second planar surface end;
the planar surface defining a data portion first end that is adjacent the first planar surface end, and a data portion extending longitudinally aft from the data portion first end to a data portion second end,
wherein the data portion includes data zones, including:
a first zone defining a first zone first end that is adjacent the data portion first end, the first zone extending longitudinally aft from the first zone first end to a first zone second end,
wherein:
the first zone defines first zone arcs, the first zone arcs being distributed in a concentric configuration,
the first zone arcs defining first mutually unique radiuses R1, ranging from a first minimum radius R1min of a first zone first arc to a first maximum radius R1max of a first zone last circle, and
wherein a concentric center of the first zone arcs is adjacent the first zone first end;
the first zone arcs are successively larger from each other by a predetermined multiplication factor;
the first zone includes first zone size markers, respectively positioned adjacent ones of the first zone arcs, and the first zone size markers respectively identify the size doubling numbers (SDNs) of the clinical lesion having a size that corresponds to a respective one of the first zone arcs, wherein the device further includes:

a slider configured to slide longitudinally along the planar surface, the slider defining a laterally extending marker, wherein a size measurement of the clinical lesion is obtained by positioning the laterally extending marker so that it laterally extends as a tangent from one of the first zone arcs corresponding to a size of the clinical lesion to a respective one of the second zone size markers, the first zone arcs are laterally aligned and longitudinally spaced apart from each other within the first zone, between the concentric center and the first zone second end; and the first zone first arc represents $2^{n1}$ volume doublings relative to a single tumor cell of the clinical lesion, and the first zone last arc represents $2^{m1}$ volume doublings relative to the single tumor cell, where $m1=n1+c1$, wherein c is the number of circles in the first zone arcs, and wherein $n1=30$, and $c1=10$ or greater;

an electronics housing connected to the slider;

an electronics controller within the slider housing;

a motion sensor operationally connected to the electronics controller and configured to sense an extent of longitudinal movement along the device, wherein the longitudinal movement is proportional to a size of the clinical lesion being measured, and one or more of:

a slider display on the slider housing that is operationally connected to the electronics controller, wherein the electronics controller, responsive to the sensing, is configured to control the slider display to provide display indicia indicative of the one or more of radius R, area A and volume V, radius doubling number, area doubling number and volume doubling number of the clinical lesion being measured; and a remote display, in wireless communication with the electronics controller, wherein the electronics controller, responsive to the sensing, is configured to control the remote display to provide display indicia indicative of the one or more of radius R, area A and volume V, radius doubling number, area doubling number and volume doubling number of the clinical lesion being measured.

6. The device of claim 5, including:

the slider display on the slider housing that is operationally connected to the electronics controller, wherein the electronics controller, responsive to the sensing, is configured to control the slider display to provide display indicia indicative of the one or more of radius R, area A and volume V, radius doubling number, area doubling number and volume doubling number of the clinical lesion being measured.

7. The device of claim 6, wherein:

the data zones include:

a second zone that is laterally adjacent the first zone, the second zone defining a second zone first end that is longitudinally aligned with the first zone, the second zone extending longitudinally aft from the second zone first end to a second zone second end, wherein:

the second zone defines a graduated line gauge and defines second zone size markers, wherein the second zone size markers identify one or more of radius R, area A, volume V, and the SDN of the clinical lesion.

8. The device of claim 7, including:

a third zone defining a third zone first end adjacent to the first zone second end, and the third zone extending longitudinally aft from the third zone first end to a third zone second end, wherein:

the third zone defines third zone circles and includes third zone size markers, the third zone circles being distributed in a non-overlapping configuration and defining second mutually unique radiuses R2 ranging from a second minimum radius R2min of a third zone first circle to a second maximum radius R2max of a third zone last circle;

each successively larger circle in the third zone circles is larger than each successively smaller circle in the third zone circles by the first multiplication factor;

the first minimum radius R1min of the first zone arcs is the same as or greater than the second maximum radius R2max of the third zone circles;

the third zone size markers identify one or more of radius R, area A, volume V and the size doubling number (SDN) of the clinical lesion having a size that corresponds to a respective one of the third zone circles.

9. The device of claim 8, wherein:

wherein the third zone first circle represents $2^{n2}$ volume doublings of the single tumor cell relative to the clinical lesion, and the third zone last circle represents $2^{m2}$ volume doublings relative to the single tumor cell, where $m2=n2+c2$, wherein c2 is the number of circles in the third zone circles, and wherein $n2=24$, and $c2=7$ or more.

10. The device of claim 9, wherein:

the device defines a ruler that is at least partially transparent, wherein the planar surface is approximately rectangular and is smaller in a lateral direction L1 than a longitudinal direction L2.

11. The device of claim 5, including:

the remote display, in wireless communication with the electronics controller, wherein the electronics controller, responsive to the sensing, is configured to control the remote display to provide display indicia indicative of the one or more of radius R, area A and volume V, radius doubling number, area doubling number and volume doubling number of the clinical lesion being measured.

12. The device of claim 11, wherein:

the data zones include:

a second zone that is laterally adjacent the first zone, the second zone defining a second zone first end that is longitudinally aligned with the first zone, the second zone extending longitudinally aft from the second zone first end to a second zone second end, wherein:

the second zone defines a graduated line gauge and defines second zone size markers, wherein the second zone size markers identify one or more of radius R, area A, volume V, and the SDN of the clinical lesion.

13. The device of claim 12, including:

a third zone defining a third zone first end adjacent to the first zone second end, and the third zone extending longitudinally aft from the third zone first end to a third zone second end, wherein:

the third zone defines third zone circles and includes third zone size markers, the third zone circles being distributed in a non-overlapping configuration and defining second mutually unique radiuses R2 ranging from a second minimum radius R2 min of a third zone first circle to a second maximum radius R2max of a third zone last circle;

each successively larger circle in the third zone circles is larger than each successively smaller circle in the third zone circles by the first multiplication factor;

the first minimum radius R1min of the first zone arcs is the same as or greater than the second maximum radius R2max of the third zone circles;

the third zone size markers identify one or more of radius R, area A, volume V and the size doubling number (SDN) of the clinical lesion having a size that corresponds to a respective one of the third zone circles.

14. The device of claim 13, wherein:

wherein the third zone first circle represents $2^{n2}$ volume doublings of the single tumor cell relative to the clinical lesion, and the third zone last circle represents $2^{-m2}$ volume doublings relative to the single tumor cell, where m2=n2+c2, wherein c2 is the number of circles in the third zone circles, and wherein n2=24, and c2=7 or more.

15. The device of claim 14, wherein:

the device defines a ruler that is at least partially transparent, wherein the planar surface is approximately rectangular and is smaller in a lateral direction L1 than a longitudinal direction L2.

* * * * *